(12) United States Patent
Forman et al.

(10) Patent No.: US 8,993,628 B2
(45) Date of Patent: Mar. 31, 2015

(54) SYNTHETIC LIGANDS SELECTIVE FOR LXRβ OVER LXRα, IDENTIFICATION AND METHODS OF USE THEREOF

(75) Inventors: Barry Forman, Irvine, CA (US); Donna Yu, Arcadia, CA (US)

(73) Assignee: City of Hope, Duarte, CA (US)

( * ) Notice: Subject to any disclaimer, the term of this patent is extended or adjusted under 35 U.S.C. 154(b) by 1943 days.

(21) Appl. No.: 12/036,050

(22) Filed: Feb. 22, 2008

(65) Prior Publication Data
US 2009/0030082 A1 Jan. 29, 2009

Related U.S. Application Data

(60) Provisional application No. 60/903,007, filed on Feb. 23, 2007.

(51) Int. Cl.
*A01N 37/12* (2006.01)
*A01N 37/44* (2006.01)
*A61K 31/195* (2006.01)
*C07C 229/00* (2006.01)
*C07C 217/18* (2006.01)

(52) U.S. Cl.
CPC ............. *A61K 31/195* (2013.01); *C07C 217/18* (2013.01)
USPC .......................................... 514/567; 562/441

(58) Field of Classification Search
CPC . A61K 31/192; A61K 31/216; A61K 31/353; A61K 45/16; A61K 2300/00; C07C 57/30; C07C 57/32
USPC .......................................... 514/567; 562/441
See application file for complete search history.

(56) References Cited

FOREIGN PATENT DOCUMENTS

WO          WO0224632    A2  *  3/2002
WO          WO 03082802  A1  *  10/2003

OTHER PUBLICATIONS

Chemical Abstract Services STN, RN 437991-39-4, Jul. 10, 2002, Abstract.*
Burns, M., K. Gaynor, V. Olm, M. Mercken, J. LaFrancois, L. Wang, P. M. Mathews, W. Noble, Y. Matsuoka & K. Duff. 2003. Presenilin redistribution associated with aberrant cholesterol transport enhances beta-amyloid production in vivo. J Neurosci. 23: 5645-9.
Cao, G., T. P. Beyer, X. P. Yang, R. J. Schmidt, Y. Zhang, W. R. Bensch, R. F. Kauffman, H. Gao, T. P. Ryan, Y. Liang, P. I. Eacho & X. C. Jiang. 2002. Phospholipid transfer protein is regulated by liver X receptors in vivo. J Biol Chem. 277: 39561-5. Epub Aug. 9, 2002.
Carstea, E. D., J. A. Morris, K. G. Coleman, S. K. Loftus, D. Zhang, C. Cummings, J. Gu, M. A. Rosenfeld, W. J. Pavan, D. B. Krizman, J. Nagle, M. H. Polymeropoulos, S. L. Sturley, Y. A. Ioannou, M. E. Higgins, M. Comly, A. Cooney, A. Brown, C. R. Kaneski, E. J. Blanchette-Mackie, N. K. Dwyer, E. B. Neufeld, T. Y. Chang, L. Liscum, D. A. Tagle & et al. 1997. Niemann-Pick C1 disease gene: homology to mediators of cholesterol homeostasis. Science. 277: 228-31.
Collins, J. L., A. M. Fivush, M. A. Watson, C. M. Galardi, M. C. Lewis, L. B. Moore, D. J. Parks, J. G. Wilson, T. K. Tippin, J. G. Binz, K. D. Plunket, D. G. Morgan, E. J. Beaudet, K. D. Whitney, S. A. Kliewer & T. M. Willson. 2002. Identification of a nonsteroidal liver X receptor agonist through parallel array synthesis of tertiary amines. J Med Chem. 45: 1963-6.
Evans, R. M., C. L. Emsley, S. Gao, A. Sahota, K. S. Hall, M. R. Farlow & H. Hendrie. 2000. Serum cholesterol, APOE genotype, and the risk of Alzheimer's disease: a population-based study of African Americans. Neurology. 54: 240-2.
Fukumoto, H., A. Deng, M. C. Irizarry, M. L. Fitzgerald & G. W. Rebeck. 2002. Induction of the cholesterol transporter ABCA1 in central nervous system cells by liver X receptor agonists increases secreted Abeta levels. J Biol Chem. 277: 48508-13.
Hirsch-Reinshagen, V., S. Zhou, B. L. Burgess, L. Bernier, S. A. McIsaac, J. Y. Chan, G. H. Tansley, J. S. Cohn, M. R. Hayden & C. L. Wellington. 2004. Deficiency of ABCA1 impairs apolipoprotein E metabolism in brain. J Biol Chem. 279: 41197-207. Epub Jul. 21, 2004.
Hoerer, S., A. Schmid, A. Heckel, R. M. Budzinski & H. Nar. 2003. Crystal structure of the human liver X receptor beta ligand-binding domain in complex with a synthetic agonist. J Mol Biol. 334: 853-61.
Horton, J. D., N. A. Shah, J. A. Warrington, N. N. Anderson, S. W. Park, M. S. Brown & J. L. Goldstein. 2003. Combined analysis of oligonucleotide microarray data from transgenic and knockout mice identifies direct SREBP target genes. Proc Natl Acad Sci U S A. 100: 12027-32. Epub Sep. 25, 2003.
Jarvik, G. P., E. M. Wijsman, W. A. Kukull, G. D. Schellenberg, C. Yu & E. B. Larson. 1995. Interactions of apolipoprotein E genotype, total cholesterol level, age, and sex in prediction of Alzheimer's disease: a case-control study. Neurology. 45: 1092-6.
Jick, H., G. L. Zornberg, S. S. Jick, S. Seshadri & D. A. Drachman. 2000. Statins and the risk of dementia. Lancet. 356: 1627-31.
Joseph, S. B. & P. Tontonoz. 2003. LXRs: new therapeutic targets in atherosclerosis? Curr Opin Pharmacol. 3: 192-7.
Joseph, S. B., E. McKilligin, L. Pei, M. A. Watson, A. R. Collins, B. A. Laffitte, M. Chen, G. Noh, J. Goodman, G. N. Hagger, J. Tran, T. K. Tippin, X. Wang, A. J. Lusis, W. A. Hsueh, R. E. Law, J. L. Collins, T. M. Willson & P. Tontonoz. 2002. Synthetic LXR ligand inhibits the development of atherosclerosis in mice. Proc Natl Acad Sci U S A. 99: 7604-9.

(Continued)

*Primary Examiner* — Sarah Pihonak
(74) *Attorney, Agent, or Firm* — Perkins Coie LLP; Yingli Wang

(57) ABSTRACT

LXR nuclear receptor agonists have been previously shown to increase cholesterol efflux, raise plasma HDL cholesterol, stimulate cholesterol excretion, and reduce atherosclerotic lesions. However, these agonists have also been associated with the unwanted side effect of hypertriglyeridemia. This hypertriglyeridemia appears to be mediated by the LXRα subtype rather than LXRβ, which suggests that LXRβ-selective agonists are attractive candidates for modulation of human lipid metabolism. The present application provides novel LXRβ-selective ligands that preferably modulate LXRβ over LXRα. These ligands may be used to treat a variety of diseases associated with LXR, such as for example lipid metabolism disorders, atherosclerosis, Alzheimer disease, and inflammation.

4 Claims, 5 Drawing Sheets

(56) References Cited

OTHER PUBLICATIONS

Koldamova, R. P., I. M. Lefterov, M. D. Ikonomovic, J. Skoko, P. I. Lefterov, B. A. Isanski, S. T. DeKosky & J. S. Lazo. 2003. 22R-Hydroxycholesterol and 9-cis-Retinoic Acid Induce ATP-binding Cassette Transporter A1 Expression and Cholesterol Efflux in Brain Cells and Decrease Amyloid beta Secretion. J Biol Chem. 278: 13244-56.

Koldamova, R. P., I. M. Lefterov, M. Staufenbiel, D. Wolfe, S. Huang, J. C. Glorioso, M. Walter, M. G. Roth & J. S. Lazo. 2004. The LXR ligand T0901317 decreases amyloid beta production in vitro and in a mouse model of Alzheimer's disease. J Biol Chem.

Laffitte, B. A., J. J. Repa, S. B. Joseph, D. C. Wilpitz, H. R. Kast, D. J. Mangelsdorf & P. Tontonoz. 2001. LXRs control lipid-inducible expression of the apolipoprotein E gene in macrophages and adipocytes. Proc Natl Acad Sci U S A. 98: 507-12. Epub Jan. 9, 2001.

Liang, Y., S. Lin, T. P. Beyer, Y. Zhang, X. Wu, K. R. Bales, R. B. DeMattos, P. C. May, S. D. Li, X. C. Jiang, P. I. Eacho, G. Cao & S. M. Paul. 2004. A liver X receptor and retinoid X receptor heterodimer mediates apolipoprotein E expression, secretion and cholesterol homeostasis in astrocytes. J Neurochem. 88: 623-34.

Neufeld, E. B., A. M. Cooney, J. Pitha, E. A. Dawidowicz, N. K. Dwyer, P. G. Pentchev & E. J. Blanchette-Mackie. 1996. Intracellular trafficking of cholesterol monitored with a cyclodextrin. J Biol Chem. 271: 21604-13.

Notkola, I. L., R. Sulkava, J. Pekkanen, T. Erkinjuntti, C. Ehnholm, P. Kivinen, J. Tuomilehto & A. Nissinen. 1998. Serum total cholesterol, apolipoprotein E epsilon 4 allele, and Alzheimer's disease. Neuroepidemiology. 17: 14-20.

Peet, D. J., S. D. Turley, W. Ma, B. A. Janowski, J. M. Lobaccaro, R. E. Hammer & D. J. Mangelsdorf. 1998. Cholesterol and bile acid metabolism are impaired in mice lacking the nuclear oxysterol receptor LXR alpha. Cell. 93: 693-704.

Plosch, T., T. Kok, V. W. Bloks, M. J. Smit, R. Havinga, G. Chimini, A. K. Groen & F. Kuipers. 2002. Increased hepatobiliary and fecal cholesterol excretion upon activation of the liver X receptor is independent of ABCA1. J Biol Chem. 277: 33870-7. Epub Jul. 8, 2002.

Repa, J. J. & D. J. Mangelsdorf. 2002. The liver X receptor gene team: potential new players in atherosclerosis. Nat Med. 8: 1243-8.

Repa, J. J., G. Liang, J. Ou, Y. Bashmakov, J. M. Lobaccaro, I. Shimomura, B. Shan, M. S. Brown, J. L. Goldstein & D. J. Mangelsdorf. 2000. Regulation of mouse sterol regulatory element-binding protein-1c gene (SREBP-1c) by oxysterol receptors, LXRalpha and LXRbeta. Genes Dev. 14: 2819-30.

Repa, J. J., S. D. Turley, J. A. Lobaccaro, J. Medina, L. Li, K. Lustig, B. Shan, R. A. Heyman, J. M. Dietschy & D. J. Mangelsdorf. 2000. Regulation of absorption and ABC1-mediated efflux of cholesterol by RXR heterodimers. Science. 289: 1524-9.

Ricote, M., A. F. Valledor & C. K. Glass. 2004. Decoding transcriptional programs regulated by PPARs and LXRs in the macrophage: effects on lipid homeostasis, inflammation, and atherosclerosis. Arterioscler Thromb Vasc Biol. 24: 230-9. Epub Oct. 30, 2003.

Runz, H., J. Rietdorf, I. Tomic, M. de Bernard, K. Beyreuther, R. Pepperkok & T. Hartmann. 2002. Inhibition of intracellular cholesterol transport alters presenilin localization and amyloid precursor protein processing in neuronal cells. J Neurosci. 22: 1679-89.

Scacchi, R., L. De Bernardini, E. Mantuano, T. Vilardo, L. M. Donini, M. Ruggeri, A. T. Gemma, R. Pascone & R. M. Corbo. 1998. DNA polymorphisms of apolipoprotein B and angiotensin I-converting enzyme genes and relationships with lipid levels in Italian patients with vascular dementia or Alzheimer's disease. Dement Geriatr Cogn Disord. 9: 186-90.

Schaefer, E. J., C. B. Blum, R. I. Levy, L. L. Jenkins, P. Alaupovic, D. M. Foster & H. B. Brewer, Jr. 1978. Metabolism of high-density lipoprotein apolipoproteins in Tangier disease. N Engl J Med. 299: 905-10.

Schaefer, E. J., D. W. Anderson, L. A. Zech, F. T. Lindgren, T. B. Bronzert, E. A. Rubalcaba & H. B. Brewer, Jr. 1981. Metabolism of high density lipoprotein subfractions and constituents in Tangier disease following the infusion of high density lipoproteins. J Lipid Res. 22: 217-28.

Schultz, J. R., H. Tu, A. Luk, J. J. Repa, J. C. Medina, L. Li, S. Schwendner, S. Wang, M. Thoolen, D. J. Mangelsdorf, K. D. Lustig & B. Shan. 2000. Role of LXRs in control of lipogenesis. Genes Dev. 14: 2831-8.

Sun, Y., J. Yao, T. W. Kim & A. R. Tall. 2003. Expression of Liver X Receptor Target Genes Decreases Cellular Amyloid {beta} Peptide Secretion. J Biol Chem. 278: 27688-27694.

Tontonoz, P. & D. J. Mangelsdorf. 2003. Liver X receptor signaling pathways in cardiovascular disease. Mol Endocrinol. 17: 985-93. Epub Apr. 10, 2003.

Vetrivel, K. S., H. Cheng, W. Lin, T. Sakurai, T. Li, N. Nukina, P. C. Wong, H. Xu & G. Thinakaran. 2004. Association of gamma-secretase with lipid rafts in post-Golgi and endosome membranes. J Biol Chem. 279: 44945-54. Epub Aug. 17, 2004.

Wahrle, S. E., H. Jiang, M. Parsadanian, J. Legleiter, X. Han, J. D. Fryer, T. Kowalewski & D. M. Holtzman. 2004. ABCA1 is required for normal central nervous system ApoE levels and for lipidation of astrocyte-secreted apoE. J Biol Chem. 279: 40987-93. Epub Jul. 21, 2004.

Wahrle, S., P. Das, A. C. Nyborg, C. McLendon, M. Shoji, T. Kawarabayashi, L. H. Younkin, S. G. Younkin & T. E. Golde. 2002. Cholesterol-dependent gamma-secretase activity in buoyant cholesterol-rich membrane microdomains. Neurobiol Dis. 9: 11-23.

Wang, L., G. U. Schuster, K. Hultenby, Q. Zhang, S. Andersson & J. A. Gustafsson. 2002. Liver X receptors in the central nervous system: from lipid homeostasis to neuronal degeneration. Proc Natl Acad Sci U S A. 99: 13878-83.

Whitney, K. D., M. A. Watson, J. L. Collins, W. G. Benson, T. M. Stone, M. J. Numerick, T. K. Tippin, J. G. Wilson, D. A. Winegar & S. A. Kliewer. 2002. Regulation of cholesterol homeostasis by the liver X receptors in the central nervous system. Mol Endocrinol. 16: 1378-85.

Williams, S., R. K. Bledsoe, J. L. Collins, S. Boggs, M. H. Lambert, A. B. Miller, J. Moore, D. D. McKee, L. Moore, J. Nichols, D. Parks, M. Watson, B. Wisely & T. M. Willson. 2003. X-ray crystal structure of the liver X receptor beta ligand binding domain: regulation by a histidine-tryptophan switch. J Biol Chem. 278: 27138-43. Epub May 7, 2003.

Wolozin, B., W. Kellman, P. Ruosseau, G. G. Celesia & G. Siegel. 2000. Decreased prevalence of Alzheimer disease associated with 3-hydroxy-3-methyglutaryl coenzyme a reductase inhibitors. Arch Neurol. 57: 1439-43.

Yamazaki, T., T. Y. Chang, C. Haass & Y. Ihara. 2001. Accumulation and aggregation of amyloid beta-protein in late endosomes of Niemann-pick type C cells. J Biol Chem. 276: 4454-60. Epub Nov. 20, 2000.

Yu, L., J. York, K. von Bergmann, D. Lutjohann, J. C. Cohen & H. H. Hobbs. 2003. Stimulation of cholesterol excretion by the liver X receptor agonist requires ATP-binding cassette transporters G5 and G8. J Biol Chem. 278: 15565-70. Epub Feb. 22, 2003.

\* cited by examiner target library

SYNTHETIC LIGANDS SELECTIVE FOR LXRβ OVER LXRα, IDENTIFICATION AND METHODS OF USE THEREOF

CROSS-REFERENCE TO RELATED APPLICATIONS

The present application claims priority to U.S. Provisional Application No. 60/903,007, filed Feb. 23, 2007, the disclosure of which is incorporated by reference herein in its entirety.

BACKGROUND

Numerous approaches have been examined for the potential treatment of Alzheimer's Disease (AD). Despite this massive effort, only two classes of drugs have been approved by the FDA for treatment of AD: cholinesterase inhibitors and memantine. Neither treatment targets the early or causative events in AD and neither is highly effective in preventing disease progression. Thus, there is a critical need for new therapies that target earlier stages of AD, and can be used as a prophylactic measure.

The two pathological hallmarks of AD are the accumulation of intracellular neurofibrillary tangles and extracellular amyloid plaques (also known as senile or neuritic plaques). The major constituent of the amyloid plaque is a peptide known as Aβ or β-amyloid[1,2], and aggregation of this peptide is now accepted as a causative factor in the disease[3]. The Aβ peptide arises via cleavage of the amyloid precursor protein (APP), a single transmembrane protein that is a substrate for several membrane bound proteases. Sequential processing by β- and γ-secretase results in production of Aβ. APP can also be cleaved by α-secretase. However, this cleavage occurs within the Aβ peptide sequence and precludes production of the amyloidogenic Aβ peptide. The opposing results of α- and β-secretase action imply that Aβ production (and AD progression) could be limited by interventions that shift APP processing away from the β-secretase pathway and/or toward α-secretase.

The processing of APP by α-secretase occurs at the cell-surface[4,5]. In contrast, β-secretase cleavage occurs within cholesterol-rich membrane domains known as lipid-rafts[6-9]. The distinct localization of the α- and β-secretase suggests that anti-amyloidogenic or α-cleavage of APP could be accentuated by retention of the APP substrate within membranes of the extracellular surface. Indeed, Aβ production is reduced when APP internalization/endocytosis is blocked by antibody-crosslinking[6]. Similarly, reduction of APP endocytosis by depletion of membrane cholesterol also attenuates Aβ production[4]. These findings suggest that AD could be treated with drugs that modulate cholesterol levels or cholesterol-trafficking in the brain.

As described above, APP processing requires an initial cleavage by either α- or β-secretase followed by a secondary cleavage with γ-secretase[3]. While the first cleavage is critical for establishing the amyloidogenic fate of APP, γ-secretase is also critical as it produces the final Aβ peptide. It appears that γ-secretase activity may also be modulated by membrane cholesterol[10,11]. For example, cholesterol content in late endosomes/lysosomes is regulated by Niemann-Pick C1 protein (NPC1), and mutations in NPC1 leads to accumulation of unesterified cholesterol in late endosomes/lysosomes[12,13]. Mice expressing the mutated NPC1 show no changes in amounts of α- or β-secretase activity but exhibit increased γ-secretase activity and accumulate Aβ[14,15]. Similarly, blockade of lysosomal cholesterol trafficking in neurons also increased γ-secretase activity[16]. Thus, reduction in membrane cholesterol content can attenuate both the β- and γ-proteolytic pathways which act sequentially to generate Aβ.

The role of cholesterol in the pathogenesis of AD and/or vascular dementia came to the forefront in 2000, when two groups independently reported that subjects that were treated with statins (3-hydroxy-3-methylglutaryl (HMG)-CoA reductase inhibitors) had a significantly lower prevalence of AD. In both studies, statins decreased AD outcome by about 70%[17,18]. Statins act by inhibiting synthesis of mevalonic acid, a rate-limiting step in cholesterol biosynthesis. In support of a specific epidemiologic connection to cholesterol, several studies have reported an association of mild hypercholesterolemia[19-22], high LDL[22-25], and low HDL levels[23,25,26] with risk for vascular dementia and AD.

Hypercholesterolemia and low HDL levels are established risk-factors for atherosclerosis and atherosclerosis is in turn associated with an increase in AD-pathology. For example, subjects who died of atherosclerotic heart disease without any other neurological diseases had a significantly greater number of amyloid plaques compared to age-matched controls without atherosclerosis[27]. The extent of arterial stenosis due to atherosclerotic plaques in large CNS blood vessels was also associated with AD[28,29]. This highlights the overlap between AD, vascular dementia and atherosclerosis.

Recent studies have demonstrated that the nuclear receptors LXRα and LXRβ are central players in cholesterol and triglyceride homeostasis[30-32]. LXRα is abundant in metabolic tissues including liver, intestine and macrophages. LXRβ is ubiquitously expressed. Both receptors bind to and are activated by cholesterol-derived oxysterol ligands. Activation of LXRs promote cholesterol efflux from many cell-types, including primary astrocyte cultures, primary neurons, and brain-derived cell-lines[33-36]. Enhanced efflux is mediated by LXR-dependent induction of cholesterol/lipid transporters from the ATP-Binding Cassette family of proteins (ABCA1, ABCG1, ABCG5 and ABCG8). These transporters stabilize and transfer cholesterol to acceptor proteins apolipoprotein-A1 (apoA1) and apolipoprotein E (apoE)[37-40]. Effects of LXR agonists against both LXRα and β are significant: they increase cellular cholesterol efflux; raise plasma HDL cholesterol; stimulate cholesterol excretion into the bile and feces, decrease hepatic cholesterol content and can reduce atherosclerotic lesions by ~50% in various murine models[41-45]. While LXR agonists against both LXRα and β appear to have significant therapeutic potential, they are undesirably associated with a clinically limiting side-effect: Treatment of C57BL/6 mice with T0901317, a LXRα/β pan-agonist induces severe hypertriglyceridemia after only 1 week of treatment[45]. Therefore, there is a need to identify and use LXR ligands which will dissociate these side-effects from the otherwise positive effects on cholesterol efflux.

Although both LXR-subtypes share a large degree of structural and functional similarity, their distinct tissue distribution profiles imply unique biological activities for each subtype. For example, LXRα knockout mice show reduced plasma triglyceride levels as well as reduced hepatic mRNA levels for enzymes of fatty acid synthesis[46]. No such effect is observed in LXRβ-null mice. Thus, the hypertriglyceridemia appears to be mediated by an LXRα-dependent activation of hepatic target genes involved in fatty acid synthesis. These target genes include Fatty Acid Synthase (FAS) and SREBP 1c[47], a master-regulator of fatty acid synthetic enzymes[48]. Conversely, ABCA1 is still induced in macrophages from LXRβ-null mice[49]. Taken together, these findings suggest that LXRα is the subtype responsible for the side-effects of hypertriglyceridemia, whereas activation of LXRβ is sufficient for the positive effects on ABCA1 transcription and macrophage cholesterol efflux.

These observations suggest LXRβ-selective agonists will be particularly useful for the modulation of human lipid metabolism. In particular, LXRβ-selective agonists will maintain the therapeutic effects of LXR activation without promoting the side-effects of hypertriglyceridemia. Therefore, there is a need to identify LXRβ-selective agonists and use LXRβ-selective agonists in the treatment of diseases associated with LXR (e.g., lipid metabolism disorders, artherosclerosis, Alzheimer disease, and inflammation[30]).

SUMMARY

In certain embodiments, LXRβ-selective ligands are provided that preferably modulate LXRβ over LXRα. Examples of LXRβ-selective ligands include, but are not limited to, T0901317, GW3965, DY136, and DY142. In certain preferred embodiments, LXRβ-selective ligands include (3-{3-[(2,2-Diphenyl-ethyl)-(2-fluoro-3-trifluoromethyl-benzyl)-amino]-propoxy}-phenyl)-acetic acid (DY136), and (3-{3-[(2,2-Diphenyl-ethyl)-(3-trifluoromethyl-benzyl)-amino]-propoxy}-phenyl)-acetic acid (DY142). In certain embodiments, pharmaceutical compositions are provided that comprise one or more LXRβ-selective ligands as disclosed herein plus a pharmaceutically acceptable carrier.

In certain embodiments, methods are provided for identifying LXRβ-selective ligands that preferably modulate LXRβ over LXRα. In certain of these embodiments, the method comprises contacting a first cell containing an LXRβ reporter gene with a test agent or a control ligand, contacting a second cell containing an LXRα reporter gene with the agent or the control ligand, measuring the expression of the reporter genes, and determining whether the test agent is an LXRβ-selective ligand, wherein the test agent is an LXRβ-selective ligand if the fold activation of LXRβ versus LXRα in the presence of the test agent is no less than the fold activation of LXRβ versus LXRα in the presence of the control ligand. In certain other embodiments, the method comprises the steps of contacting a first cell with a test agent, measuring fold activation of an LXRβ gene and an LXRα gene in the presence of the test agent; contacting a second cell with a positive control ligand, measuring activation of the LXRβ gene and the LXRα gene in the presence of the positive control ligand, and determining whether the test agent is an LXRβ-selective ligand, wherein the test agent is an LXRβ-selective ligand if the activation of an LXRβ gene in the presence of the test agent is higher relative to when in the presence of the control ligand and the activation of a LXRα gene in the presence of the test agent is lower relative to when in the presence of the control ligand.

In certain embodiments, methods are provided for modulating, such as for example reducing, an amyloidogenic effect in a cell or a subject. In certain of these embodiments, the method comprises the steps of contacting a cell with one or more LXRβ-selective ligands. The amyloidogenic effect may be reduced by, for example, reducing Aβ production, inducing ABCA1, inducing non-amyloidogenic processing of APP, and/or increasing amyloid clearance. Contacting a cell with an LXRβ-selective ligand may reduce the amyloidogenic effect by any one of these methods, or by a combination of one or more of these methods. Therefore, in certain embodiments, methods are provided for reducing Aβ production, inducing ABCA1, inducing non-amyloidogenic processing of APP, and/or increasing amyloid clearance in a cell by contacting the cell with one or more LXRβ-selective ligands.

In certain embodiments, methods are provided for treating or preventing LXRβ associated disorders by administering one or more LXRβ-selective ligands to a subject. In certain of these embodiments, the LXRβ associated disorder being treated may be, for example, atherosclerosis, Alzheimer's disease, or inflammation.

DETAILED DESCRIPTION

Figure 1:
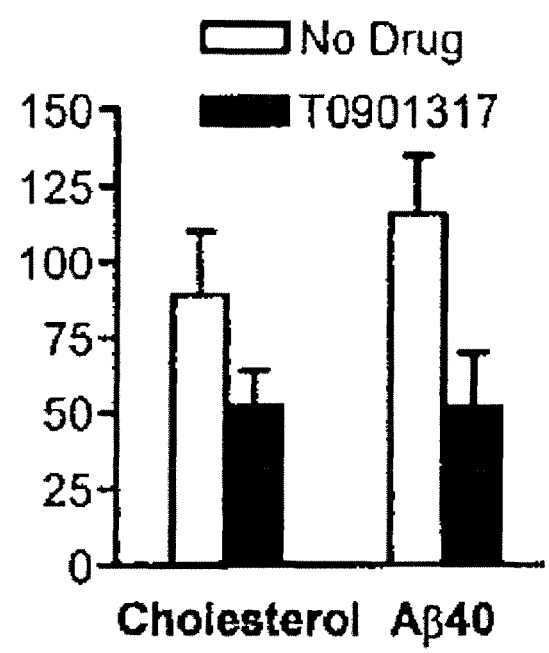
FIG. 1 shows the level of cholesterol and Aβ40 in human H4 neuroglioma cells in the presence or absence of an LXR agonist T0901317.

One aspect of the present invention relates to LXRβ-selective ligands. The term LXRβ-selective ligands (agonists or antagonists) refers to any compound(s) that modulates (e.g., regulates, activates, or reduces) LXRβ more effectively than LXRα, or to any compound(s) which preferentially modulates LXRβ more than LXRα. LXRβ-selective ligands possess one or more of the following features: 1) higher fold activation of LXRβ/LXRα than that of T0901317 or GW3965 in a reporter gene assay described herein; 2) strong stimulation of ABC-transporters and cholesterol efflux; 3) minimal induction of LXRα specific genes (e.g., SREBP1c and FAS); 4) siRNAs directed at LXRβ lower the ABCA1/cholesterol-efflux stimulation caused by LXRβ-selective ligands; and 5) glial cultures from LXRβ-knockout fail to respond (or respond poorly) to LXRβ-selective ligands.

Examples of LXRβ-selective ligands include, but are not limited to, T0901317, GW3965, (3-{3-[(2,2-Diphenyl-ethyl)-(2-fluoro-3-trifluoromethyl-benzyl)-amino]-propoxy}-phenyl)-acetic acid (DY136), and (3-{3-[(2,2-Diphenyl-ethyl)-(3-trifluoromethyl-benzyl)-amino]-propoxy}-phenyl)-acetic acid (DY142). In a preferred embodiment, LXRβ-selective ligands include DY136 and DY142. Such ligands can be used as control ligands (i.e., positive controls).

Another aspect of the present invention relates to methods of identifying LXRβ-selective ligands. In one embodiment, the method comprises the steps of contacting a first cell containing an LXRβ reporter gene with a test agent or a control ligand, contacting a second cell containing an LXRα reporter gene with the agent or the control ligand, measuring the expression of the reporter genes, and determining whether the test agent is an LXRβ-selective ligand. A control ligand includes those compound(s) or ligands suitable for use as a positive control or having a known LXR-selective activity. A test agent is an LXRβ-selective ligand if the fold activation of LXRβ versus LXRα in the presence of the test agent is no less than the fold activation of LXRβ versus LXRα in the presence of the control ligand. A reporter gene is generally any gene whose product is easily detected. A reporter gene may be any gene or sequence of a gene that is easily observed, measured or identified when it is expressed in a given cell, tissue or at a certain stage of development, or a gene whose phenotypic expression is easy to monitor. A recombinant DNA construct can be made in which the LXRβ or LXRα reporter gene is attached to a suitable promoter and the LXRβ-reporter or LXRα-reporter construct is transfected into a cell or organism. The test agent or putative selective ligand is then applied and the expression of LXRβ by the LXRβ-reporter transfected cell is measured and compared to the expression of LXRα by the LXRα-reporter transfected cell to determine whether the test agent is a selective ligand. Reporter activity analyzed after transfection may be measured as activation or fold activation relative to the basal level of reporter gene(s) in the presence of control ligand. Methods for constructing reporter genes and their use are known in the art and described for example in Sambrook et al., Molecular Cloning: A Laboratory Manual, $2^{nd}$ Ed., Cold Spring Harbor Laboratory Press, Cold Spring Harbor, N.Y.

In another embodiment, the method comprises the steps of contacting a first cell with a test agent, measuring fold activation of an LXRβ gene and an LXRα gene in the presence of the test agent; contacting a second cell with a control ligand, measuring activation of the LXRβ gene and the LXRα gene in the presence of the control ligand, and determining whether the test agent is an LXRβ-selective ligand, wherein the test agent is an LXRβ-selective ligand if the activation of an LXRβ gene in the presence of the test agent is higher relative to the presence of the control ligand and the activation of an LXRα gene in the presence of the test agent is lower relative to the presence of the control ligand.

A control ligand includes T0901317, GW3965, or a known LXRβ-selective ligand. An LXRβ-selective ligand includes DY136 and DY142. An LXRβ target gene is a gene whose expression is induced or inhibited when LXRβ is activated. An LXRα target gene is a gene whose expression is induced or inhibited when LXRα is activated. Examples of LXRα and LXRβ target genes include an ATP binding cassette (ABC) gene, ABCA1, ABC G1/G4/G5/G8, SR-BI, apoE, apoCII, PLTP, VEGF, sterol regulatory element binding protein 1c (SREPB-1c), fatty acid synthase (FAS), acyl coenzyme A carboxylase (ACC), LPL, Angiopoietin-like prot 3, GLUT4 (fat only), AIM (apoptosis inhibitor expressed by macrophages; also called Spá or Api6), sterol coenzyme A desaturase 1 (SCD-1).

A test agent may be any compound or drug that is subject to the identification test. A test agent may be selected from the group consisting of (3-Hydroxy-phenyl)-acetic acid methyl ester; [3-(3-Bromo-propoxy)-phenyl]-acetic acid methyl ester; {3-[3-(2,2-Diphenyl-ethylamino)-propoxy]-phenyl}-acetic acid methyl ester; (3-{3-[(2,2-Diphenyl-ethyl)-(2-fluoro-3-trifluoromethyl-benzyl)-amino]-propoxy}-phenyl)-acetic acid methyl ester; (3-{3-[(2,2-Diphenyl-ethyl)-(2,3-difluoro-benzyl)-amino]-propoxy}-phenyl)-acetic acid methyl ester; (3-{3-[(2,2-Diphenyl-ethyl)-(3-trifluoromethoxy-benzyl)-amino]-propoxy}-phenyl)-acetic acid methyl ester; (3-{3-[(2,2-Diphenyl-ethyl)-(3-methoxy-benzyl)-amino]-propoxy}-phenyl)-acetic acid methyl ester; (3-{3-[(2,2-Diphenyl-ethyl)-(3,5-bis(trifluoromethyl)-benzyl)-amino]-propoxy}-phenyl)-acetic acid methyl ester; (3-{3-[(2,2-Diphenyl-ethyl)-(3-iodo-benzyl)-amino]-propoxy}-phenyl)-acetic acid methyl ester; (3-{3-[(2,2-Diphenyl-ethyl)-(3-trifluoromethyl-benzyl)-amino]-propoxy}-phenyl)-acetic acid methyl ester; (3-{3-[(2,2-Diphenyl-ethyl)-(3-chloro-benzyl)-amino]-propoxy}-phenyl)-acetic acid methyl ester; (3-{3-[(2,2-Diphenyl-ethyl)-(3,5-di-tert-butyl-benzyl)-amino]-propoxy}-phenyl)-acetic acid methyl ester; (3-{3-[(2,2-Diphenyl-ethyl)-(3,5-dimethoxy-benzyl)-amino]-propoxy}-phenyl)-acetic acid methyl ester; (3-{3-[(2,2-Diphenyl-ethyl)-(2,3-difluoro-benzyl)-amino]-propoxy}-phenyl)-acetic acid (DY137); (3-{3-[(2,2-Diphenyl-ethyl)-(3-trifluoromethoxy-benzyl)-amino]-propoxy}-phenyl)-acetic acid (DY138); (3-{3-[(2,2-Diphenyl-ethyl)-(3-methoxy-benzyl)-amino]-propoxy}-phenyl)-acetic acid (DY139); (3-{3-[(2,2-Diphenyl-ethyl)-(3,5-bis(trifluoromethyl)-benzyl)-amino]-propoxy}-phenyl)-acetic acid (DY140); (3-{3-[(2,2-Diphenyl-ethyl)-(3-iodo-benzyl)-amino]-propoxy}-phenyl)-acetic acid (DY141); (3-{3-[(2,2-Diphenyl-ethyl)-(3-chloro-benzyl)-amino]-propoxy}-phenyl)-acetic acid (DY143); (3-{3-[(2,2-Diphenyl-ethyl)-(3,5-di-tert-butyl-benzyl)-amino]-propoxy}-phenyl)-acetic acid (DY151); (3-{3-[(2,2-Diphenyl-ethyl)-(3,5-dimethoxy-benzyl)-amino]-propoxy}-phenyl)-acetic acid (DY152).

Another aspect of the present invention relates to methods of modulating (e.g., reducing) an amyloidogenic effect in a cell or a subject. In one embodiment, the method comprises the steps of contacting a cell with an LXRβ-selective ligand. Examples of reducing amyloidogenic effects include a reduction in Aβ production, an induction of ABCA1, an induction of non-amyloidogenic processing of APP, and an increase of amyloid clearance.

Another aspect of the present invention relates to methods of treating or preventing LXRβ associated disorders by administering an LXRβ-selective ligand to a subject. In one embodiment, examples of the LXRβ associated disorders include atherosclerosis, Alzheimer disease, and inflammation.

This invention also provides a method for treating a LXR-selective ligand associated disorder in a subject, which comprises administering to the subject an amount of the pharmaceutical composition comprising LXR-selective ligand to thereby treat a disorder associated with the LXR-selective ligand.

The invention also relates to pharmaceutical compositions comprising an effective amount of a composition as described herein, in admixture with a pharmaceutically acceptable carrier. The term "pharmacologically active" means that a substance so described is determined to have activity that affects a medical parameter (e.g., blood pressure, blood cell count, cholesterol level) or disease state (e.g., arteriosclerosis, heart disease, vascular disease, autoimmune disorders, etc.).

When administered to a subject, the LXR-selective ligand of the invention is administered as a pharmaceutical composition containing, for example, the LXR-selective ligand and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil or injectable organic esters, or emulsions such as oil/water emulsions or a triglyceride emulsion, various types of wetting agents, tablets, coated tablets and capsules. A suitable pharmaceutically acceptable carrier may be selected taking into account the chosen mode of administration.

A pharmaceutically acceptable carrier can also contain physiologically acceptable compounds that act, for example, to stabilize or to increase the absorption of the conjugate. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art will know that the choice of a pharmaceutically acceptable carrier, including a physiologically acceptable compound, depends, for example, on the route of administration of the composition.

One skilled in the art will know that a pharmaceutical composition containing an LXR-selective ligand of the invention can be administered to a subject by various routes including, for example, orally or parenterally, such as intravenously. The composition can be administered by injection or by intubation. The pharmaceutical composition also can be an antibody linked to liposomes or other polymer matrices, which can have incorporated therein, for example, a drug such as a chemotherapeutic agent (Gregoriadis, Liposome Technology, Vols. I to III, 2nd ed. (CRC Press, Boca Raton Fla. (1993), which is incorporated herein by reference). Liposomes, for example, which consist of phospholipids or other lipids, are nontoxic, physiologically acceptable and metabolizable carriers that are relatively simple to make and administer.

The invention includes the pharmaceutically acceptable salts and complexes of all the compounds described herein. The salts include but are not limited to the following acids and bases. Examples of suitable inorganic acids include, but are not limited to: hydrochloric acid, hydrofluoric acid, hydrobromic acid, hydroiodic acid, sulfuric acid and boric acid. Examples of suitable organic acids include but are not limited to: acetic acid, trifluoroacetic acid, formic acid, oxalic acid, malonic acid, succinic acid, tartaric acid, maleic acid, fumaric acid, methanesulfonic acid, trifluoromethanesulfonic acid, benzoic acid, glycolic acid, lactic acid, citric acid and mandelic acid. Examples of suitable inorganic bases include, but are not limited to: ammonia, hydroxyethylamine and hydrazine. Examples of suitable organic bases include, but are not limited to, methylamine, ethylamine, trimethylamine, triethylamine, ethylenediamine, hydroxyethylamine, morpholine, piperazine and guanidine. The invention further provides for the hydrates and polymorphs of all of the compounds described herein.

In one preferred embodiment, the pharmaceutical carrier may be a liquid and the pharmaceutical composition would be in the form of a solution. In another equally preferred embodiment, the pharmaceutically acceptable carrier is a solid and the pharmaceutical composition is in the form of a powder or tablet. In a further embodiment, the pharmaceutical carrier is a gel and the pharmaceutical composition is in the form of a suppository or cream. In a further embodiment, the compound may be formulated as part of a pharmaceutically acceptable transdermal patch.

A solid carrier can include one or more substances which may also act as flavoring agents, lubricants, solubilizers, suspending agents, fillers, glidants, compression aids, binders or table-disintegrating agents, it can also be an encapsulating material. In powders, the carrier is a finely divided solid that is in admixture with the finely divided active ingredient. In tablets, the active-ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Besides containing an effective amount of the compounds described herein the pharmaceutical compositions may also include suitable diluents, preservatives, solubilizers, emulsifiers, adjuvant and/or carriers.

The compound can be administered in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The choice of composition will depend on the physical and chemical properties of the compounds. Controlled or sustained release compositions include formulation of lipophilic deposits (e.g., fatty acids, waxes, oils). Also comprehended by the invention are particulate compositions coated with polymers (e.g., poloxamers or poloxamines) and compounds coupled to antibodies directed against tissue-specific receptors, ligands or antigens or coupled to ligands of tissue-specific receptors. Other embodiments of the compositions of the invention incorporate particulate forms of protective coatings, protease inhibitors or permeation enhancers for various routes of administration, including parenteral, pulmonary, nasal and oral.

Optimal dosages to be administered may be determined by those skilled in the art, and will vary with the particular compound in use, the strength of the preparation, the mode of administration, and the advancement of the disease condition. Additional factors depending on the particular subject being treated, including subject age, weight, gender, diet and time of administration, will result in a need to adjust dosages. Administration of the compound may be effected continuously or intermittently. in any treatment regimen, the composition may be administered to a patient either singly or in a cocktail containing two or more targeted toxins, other therapeutic agents, compositions, or the like, including, but not limited to, immunosuppressive agents, tolerance-inducing agents, potentiators and side-effect relieving agents. Preferred immunosuppressive agents include prednisone, prednisolone, DECADRON (Merck, Sharp & Dohme, West Point, Pa.), cyclophosphamide, cyclosporine, 6-mercaptopurine, methotrexate, azathioprine and i.v. gamma globulin or their combination. Preferred potentiators include monensin, ammonium chloride, perhexyline, verapamil, amantadine, and chloroquine. All of these agents are administered in generally-accepted efficacious dose ranges such as those disclosed in the Physician's Desk Reference, 41st Ed., Publisher Edward R. Barnhart, N.J. (1987).

In the treatment, an appropriate dosage level will generally be about 0.001 to 50 mg per kg patient body weight per day that can be administered in single or multiple doses. Preferably, the dosage level will be about 0.005 to about 25 mg/kg, per day; more preferably about 0.01 to about 10 mg/kg per day; and even more preferably about 0.05 to about 1 mg/kg per day.

Additional pharmaceutical compositions will be evident to those skilled in the art, including formulations involving binding agent molecules in sustained- or controlled-delivery formulations. Techniques for formulating a variety of other sustained- or controlled-delivery means, such as liposome carriers, bio-erodible microparticles or porous beads and depot injections, are also known to those skilled in the art. See for example, PCT/US93/00829 that describes controlled release of porous polymeric microparticles for the delivery of pharmaceutical compositions. Additional examples of sustained-release preparations include semipermeable polymer matrices in the form of shaped articles, e.g. films, or microcapsules. Sustained release matrices may include polyesters, hydrogels, polylactides (U.S. Pat. No. 3,773,919, EP 58,481), copolymers of L-glutamic acid and gamma ethyl-L-glutamate [Sidman et al., Biopolymers, 22:547-556 (1983)], poly (2-hydroxyethyl-methacrylate) [Langer et al., J. Biomed. Mater. Res., 15:167-277, (1981)] and [Langer et al., Chem. Tech., 12:98-105 (1982)], ethylene vinyl acetate (Langer et al., supra) or poly-D(-)-3-hydroxybutyric acid (EP 133,988). Sustained-release compositions also include liposomes, which can be prepared by any of several methods known in the art. See e.g., Eppstein et al., Proc. Natl. Acad. Sci. (USA), 82:3688-3692 (1985); EP 36,676; EP 88,046; EP 143,949.

In one embodiment, the present invention is directed to kits for producing a single-dose administration unit. The kits may each contain both a first container having a dried protein and a second container having an aqueous formulation. Also included within the scope of this invention are kits containing single and multi-chambered pre-filled syringes (e.g., liquid syringes and lyosyringes).

An effective amount of a pharmaceutical composition to be employed therapeutically will depend, for example, upon the therapeutic context and objectives. One skilled in the art will appreciate that the appropriate dosage levels for treatment will thus vary depending, in part, upon the molecule delivered, the indication for which the LXR-selective ligand is being used, the route of administration, and the size (body weight, body surface or organ size) and condition (the age and general health) of the patient. Accordingly, the clinician may titer the dosage and modify the route of administration to obtain the optimal therapeutic effect. A typical dosage may range from about 0.1 mg/kg to up to about 100 mg/kg or more, depending on the factors mentioned above. In other embodiments, the dosage may range from 0.1 mg/kg up to about 100 mg/kg; or 1 mg/kg up to about 100 mg/kg; or 5 mg/kg up to about 100 mg/kg.

The exact dosage will be determined in light of factors related to the subject requiring treatment. Dosage and administration are adjusted to provide sufficient levels of the active compound or to maintain the desired effect. Factors that may be taken into account include the severity of the disease state, the general health of the subject, the age, weight, and gender of the subject, time and frequency of administration, drug combination(s), reaction sensitivities, and response to therapy. Long-acting pharmaceutical compositions may be administered every 3 to 4 days, every week, or biweekly depending on the half-life and clearance rate of the particular formulation.

The frequency of dosing will depend upon the pharmacokinetic parameters of the LXR-selective ligand in the formulation used. Typically, a composition is administered until a dosage is reached that achieves the desired effect. The composition may therefore be administered as a single dose, or as multiple doses (at the same or different concentrations/dosages) over time, or as a continuous infusion. Further refinement of the appropriate dosage is routinely made. Appropriate dosages may be ascertained through use of appropriate dose-response data.

EXAMPLES

Example 1

Figure 2:
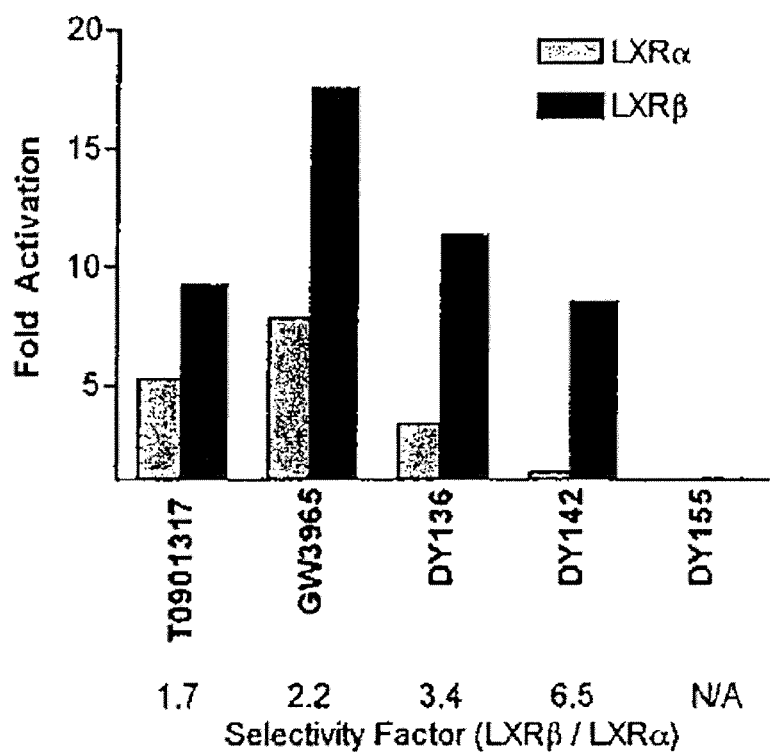
FIG. 2 shows the chemical structures of LXR ligands (T0901317, GW3965, DY136, DY142, DY155), their effect on the activity of LXRβ and LXRα, and the fold activation of LXRβ versus LXRα in the presence of each ligand.
Figure 2:
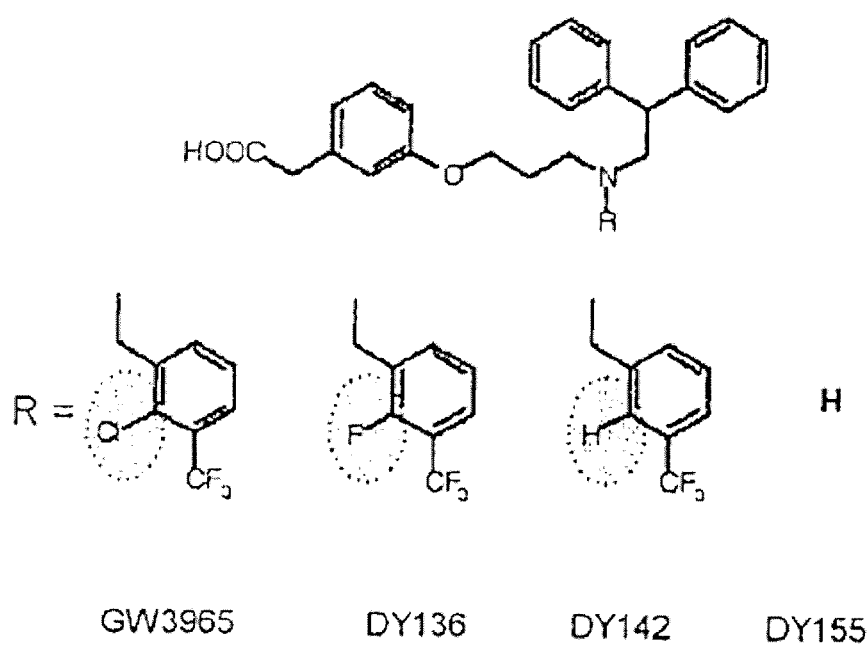

Effect of LXR Ligand T0901317 on Gene Expression, Cellular Cholesterol Content, and Aβ Accumulation In order to confirm the effects of LXR activation on Aβ production in human cells, human H4 neuroglioma cells were treated with the pan-LXR agonist T0901317 (1 µM) for 24 hours and measured the amount of total cellular cholesterol remaining in the cells and the amount of Aβ40 secreted into the media (FIG. 1). As expected, T0901317 reduced both intracellular cholesterol levels as well as secreted Aβ40. The lack of significant amounts of intracellular Aβ40 indicated that the amount of secreted Aβ40 represents a very close approximation of total Aβ40 levels. Also as expected, T0901317 induced a greater than 50-fold increase in ABCA1 expression in H4 cells (FIG. 2). These results confirm the results of other labs and further demonstrate that LXR ligands decrease Aβ production in association with an ABCA1-mediated increase in cholesterol efflux[36,52].

For quantification of total cellular cholesterol, H4 cells are seeded in 12-well plates at 70,000 per well. Cells are treated with DMSO (vehicle) or T0901317 in serum-free DMEM for 24 hours in presence of 10 µg/ml apoA1. Cells were lysed with 1N NaOH in 90% ethanol and 10 µM of 5α-cholestane as an internal control tracer. Cholesterol esters were hydrolyzed by incubation at 65° C. for 2 hours. Equal volume of water is added to the samples, and extracted twice with 2 volumes of hexane. The organic phase was collected, pooled and dried under a stream of nitrogen. The samples were silylated with BSTFA+1% TMCS (Pierce) at 55° C. for 6 hours and analyzed by gas chromatography-mass spectrometry (GC-MS).

To quantify Aβ production, cells were cultured as described above (gene expression analysis). Media was added to the diluent Buffer provided with the kit and assayed according to the manufacturer's instructions (Biosource).

Example 2

Identification of Novel LXRβ-Selective Ligands

Several potential LXR ligands were synthesized as described in Example 5. These compounds were assayed for activity on human LXRα and LXRβ using high-throughput reporter gene assays (e.g., reporter gene assays using Biomek automated workstation) in transiently transfected CV-1 cells. As expected, the pan LXR agonists T0901317 and GW3965 activated both LXRα and LXRβ. In addition, two novel LXR agonists (DY136 and DY142) were identified. Both DY136 and DY142 exhibited several fold selectivity for LXRβ over LXRα (FIG. 2, left; $EC_{50}$=1-3 µM). Examination of LXRβ-selectivity, calculated as fold activation of LXRβ/LXRα, indicated that T0901317 and GW3965 (10 µM) have LXRβ-selectivity factors of 1.7 and 2.2 respectively, whereas DY136 (10 µM) and D142 (10 µM) display enhanced LXRβ-selectivity with factors of 3.4 and 6.5. Analysis of the structure of the identified compounds suggests that the smaller the R group, the greater the selectivity for LXRβ. The ortho (2-benzyl) position of the R group appears critical, with LXRβ-selectivity following the pattern of H>F>Cl (FIG. 2, right, dotted grey circles).

In the reporter gene assay CV-1 cells were grown in Dulbecco's Modified Eagle's medium supplemented with 10% resin-charcoal stripped fetal bovine serum, 50 U/ml penicillin G and 50 µg/ml streptomycin sulfate (DMEM-FBS) at 37° C. in 5% $CO_2$. One day prior to transfection, cells were plated to 50-80% confluence using phenol-red free DMEM-FBS. Cells were transiently transfected by lipofection with DOTAP. A GAL4 luciferase reporter construct (300 ng/$10^5$ cells) and cytomegalovirus driven expression vectors for GAL4-LXRα or GAL4-LXRβ (20-50 ng/$10^5$ cells) were added along with CMX-βgal (500 ng/$10^5$ cells) as an internal control. After 2 hours the liposomes were removed and cells treated for approximately 45 hours with phenol-red free DMEM-FBS containing the indicated LXR ligands. After exposure to ligand, the cells were harvested and assayed for luciferase and β-galactosidase activity. All points were assayed in triplicate. Each experiment was repeated three or more times with similar results. Use of reporter gene assays are known in the art and described for example in Sambrook et al., Molecular Cloning: A Laboratory Manual, 2$^{nd}$ Ed., Cold Spring Harbor Laboratory Press, Cold Spring Harbor, N.Y.

Example 3

Gene Expression Profile for Novel LXR Ligands

Figure 3:
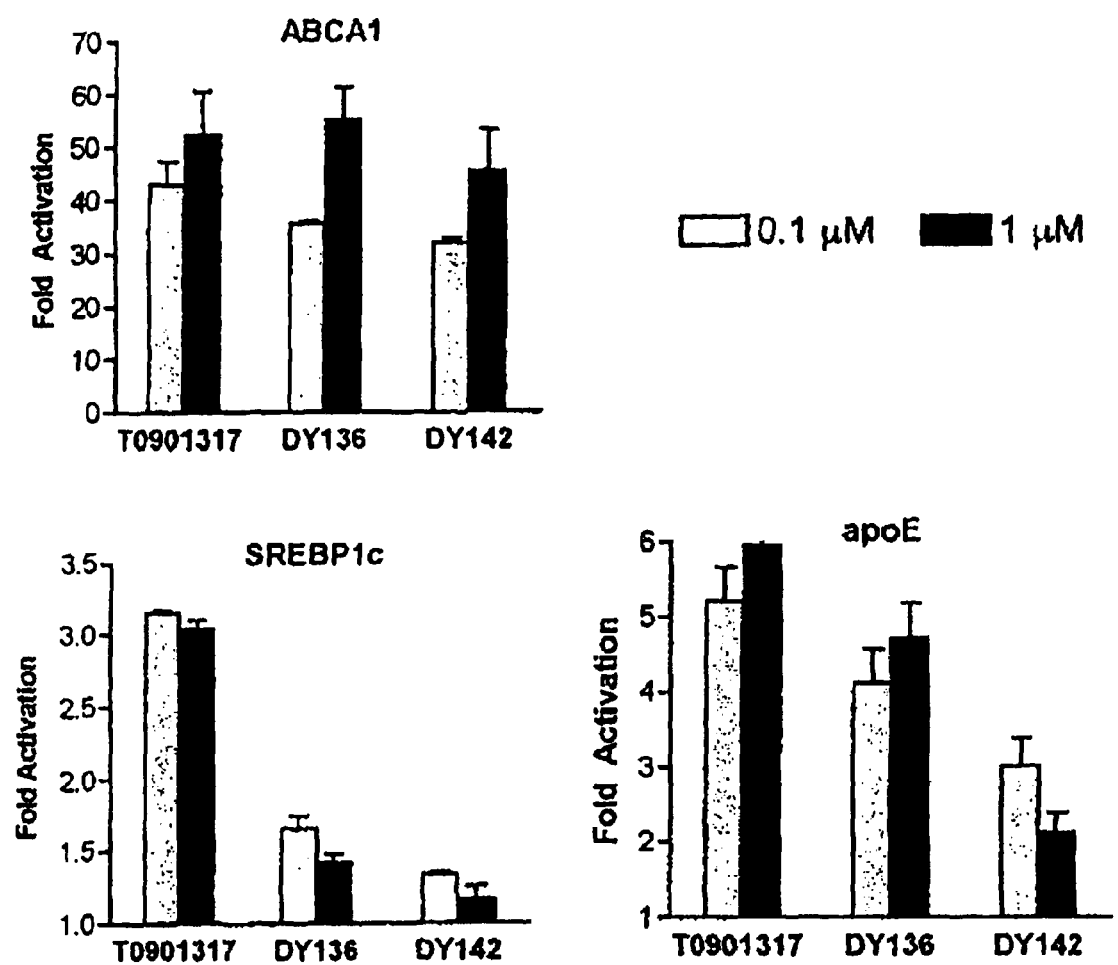
FIG. 3 shows the effect of LXR ligands (T0901317, DY136 and DY142) on the expression of ABCA1, SREBP1c and apoE.

The effect of various concentrations of LXRβ-selective compounds on endogenous LXR target genes in H4 cells was examined. Both DY136 and DY142 induced ABCA1 expression in H4 neuroglioma cells to a level nearly that of the pan-agonist T0901317 (FIG. 3, left). Induction of ABCG1, another lipid-transporter regulated by LXR, was also observed in H4 cells treated with T0901317, DY136 and DY142. In sharp contrast, induction of SREBP1c by DY136 and DY142 was only half that observed with T0901317 (FIG. 3, center). ApoE expression was also increased by all three ligands, although the effects were slightly lower for DY142 (FIG. 3, right). Initial data from differentiated THP-1 (human macrophage) and CCF-STTG1 (human astrocytoma) cells showed a similar pattern of activity.

Gene expression analysis was conducted to measure the endogenous LXR target genes. Briefly, cells were plated in a 6-well plate at the following densities/well: 0.35 million H4 cells (DMEM, 10% FBS), 0.5 million CCF-STTG1 (RPMI, 15% FBS), 1 million SH-SY5Y (RPMI, 15% FBS), or 1 million THP (RPMI, 15% FBS+100 nM TPA for 3 days to differentiate). The cells were treated the next day in serum-free DMEM supplemented with insulin, transferrin, and selenium and apoA1 (10 µg/ml). The media was harvested 24 hours later, mixed with a protease inhibitor cocktail (Roche), debris was pelleted (14000 g, 5 min.) and the supernatant saved for Aβ measurements (below). The cells were then rinsed with PBS and lysed with Trizol reagent. RNA isolation and cDNA synthesis (OmniScript, Qiagen) were as per manufacturer's protocol. Gene expression analysis was done in triplicate with 30 ng of cDNA and the following primer-sets: ABCA1, ABCG1, SREBP1c, GAPDH, HPRT (either SYBR Green or FAM-labeled LUX primers (Invitrogen). None of these primers produce primer-dimers or amplified genomic DNA (all primer-sets are intron spanning). The signal for each target gene was normalized to GAPDH and/or HPRT.

Example 4

Design of LXRβ-Selective Compounds

As shown above, using the non-selective agonist GW3965 as a template, two novel compounds were identified that were 3.4-6.5 fold selective for LXRβ over LXRα (FIG. 2). These compounds display the beneficial effect of inducing ABCA1 without the unwanted side-effect of inducing SREBP1c. Additional LXRβ-selective compounds may be identified using similar screening methods. Ligands identified in these screens may exhibit higher affinity and/or higher selectivity for LXRβ.

The rationale for design of additional LXRβ-selective compounds reflects the observation that the smaller the ortho substituent of the 3-trifluoromethyl-benzyl R group (FIG. 2), the greater the selectivity for LXRβ, while substitutions at the meta and para positions resulted in loss of agonist activity. We initially attempted to account for this selectivity by examining the crystal structure of LXRβ complexed with the parent ligand GW3965[55,56]. Unfortunately, the corresponding LXRα-GW3965 structure has not been reported and the LXRβ subpocket surrounding the critical 2-chloro-3-trifluoromethyl-benzyl R-group (FIG. 2) is very similar to its LXRα counterpart. This raises the possibility that DY136 and D142 may generate selectivity by promoting a ligand-induced "fit" that is unique to these compounds. Whatever the mechanism, it appeared that molecular modeling would not be a useful design tool in this instance. Thus, the most feasible path to develop new compounds appears to be an empirical approach that takes advantage of the observation that LXRβ selectivity increases as the ortho-substituent of the trifluoromethyl-benzyl R-group decreases in size. Thus, a small "library" of R-groups containing 5-membered rings will be synthesized and tested for their selectivity for LXRβ.

Figure 4:
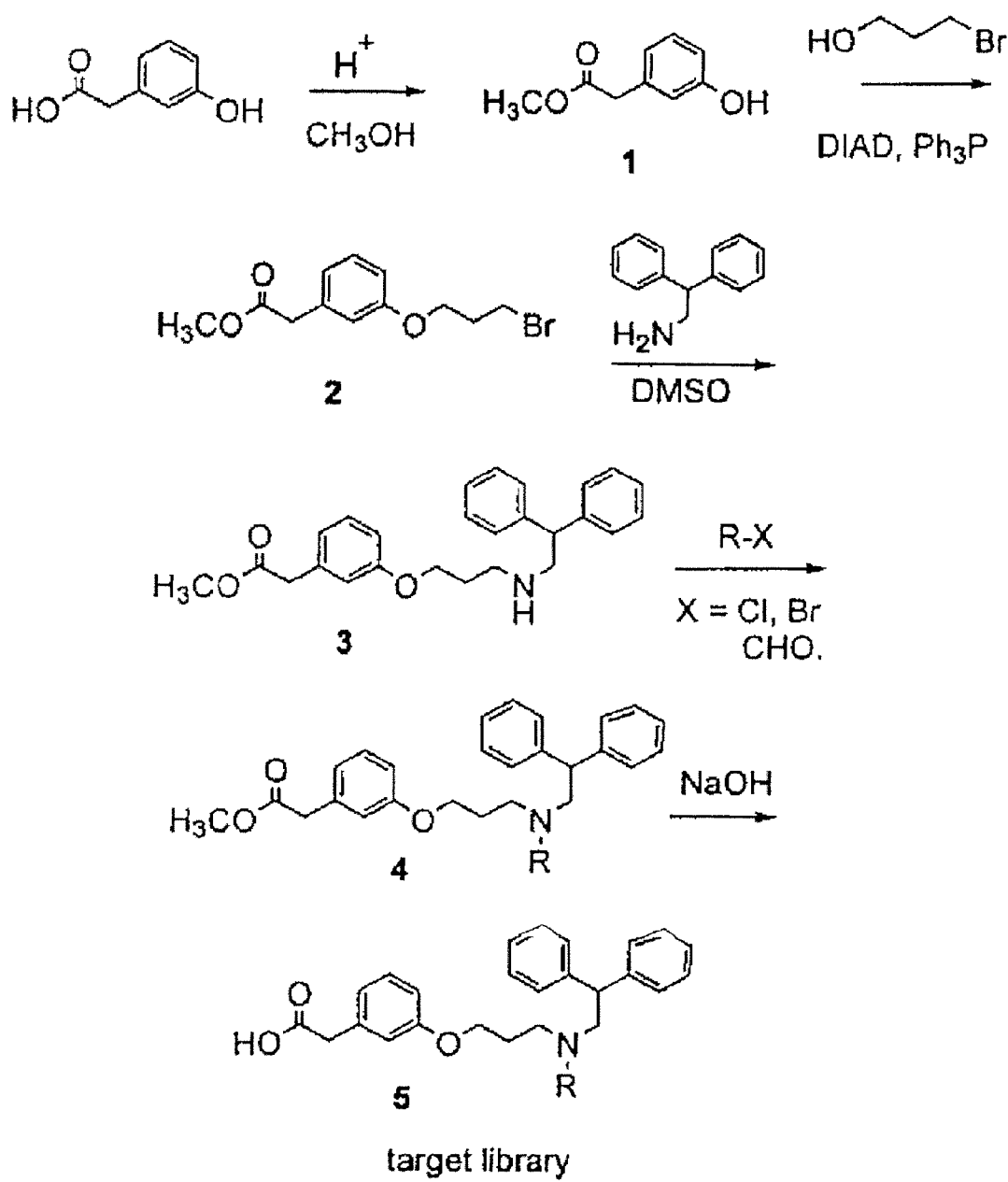
FIG. 4 shows a schematic outline for the synthesis of the {3-(3-[(2,2-diphenyl-ethylamino)-propoxy]-phenyl}-acetic acid (5) compound library.

The scheme in FIG. 4 outlines the general screening procedure, which is essentially the same as the procedure used to identify DY136 and DY142. The final target compounds are described by compound 5, which will vary based on the particular R-group that is linked to the tertiary amine.

To increase the likelihood of "druggability", specific R groups were selected such that the final compounds adhere to Lipinski's rules (molecular weights<500 Da, calculated octanol/water partition coefficients (ClogP)<5 and less than 5H-bond donors and 10H-bond acceptors)[57]. Additional selection criteria included chemical compatibility, structure diversity, inclusion of drug-like substructures and commercial availability whenever possible.

Example 5

Synthesis of [3-(3-[(2,2-diphenyl-ethylamino)-propoxy]-phenyl]-acetic acid (5)

As shown in FIG. 4, 3-hydroxyphenyl acetic acid (commercially available) will be esterified to obtain (3-hydroxyphenyl)-acetic acid methyl ester 1. Compounds 2 through 3 will be synthesized according to the method of Collins et al.[58]. The phenolic acid methyl ester 1 will react with 3-bromopropanol under Mitsunobu conditions to generate compound 2. The bromide intermediate 2 will be treated with a solution of diphenylethylamine in DMSO to yield compound 3 which will fix the secondary amine template. This secondary amine template 3 will be subjected to a series of R substituents by a parallel synthesis methodology with an automated Bohdan synthesizer to give 4. Ninety-six different potential compounds have been chosen as R groups. The compound 4 will be achieved by means of reductive amination and nucleophilic substitution, which are well-known synthetic methods to prepare high yield tertiary amines. By these two methods, compounds 3 will be transferred to a series of tertiary amine ester derivatives 4 which will have a set of different R substituents introduced at the N position. In the final step, saponification of compound 4 with NaOH/MeOH will generate a series of carboxylic acids designated as compound 5. A Biotage Quad 3 automated medium pressure flash chromatography system will be used for the parallel purification. The solvent will be removed by a Savant solvent concentrator and evaporated under reduced pressure. Compounds will be analyzed by NMR (500-600 MHz) with an autosampler. This procedure will facilitate sample analyses and give rapid structure determinations.

To perform these procedures rapidly, the reaction series of 4 and 5 will be carried out in a Bohdan automated synthesizer. This screw-synthesizer is an ideal device for rapidly achieving the proposed parallel solution-phase reaction as 48-reactions can be performed simultaneously. A Biotage Quad 3 automated medium pressure flash chromatograph will be used for the parallel purification. This unit can perform 12 simultaneous flash chromatographs using prepacked silica gel columns. Twenty fractions can be easily obtained from each run in under 20 minutes.

Figure 5:
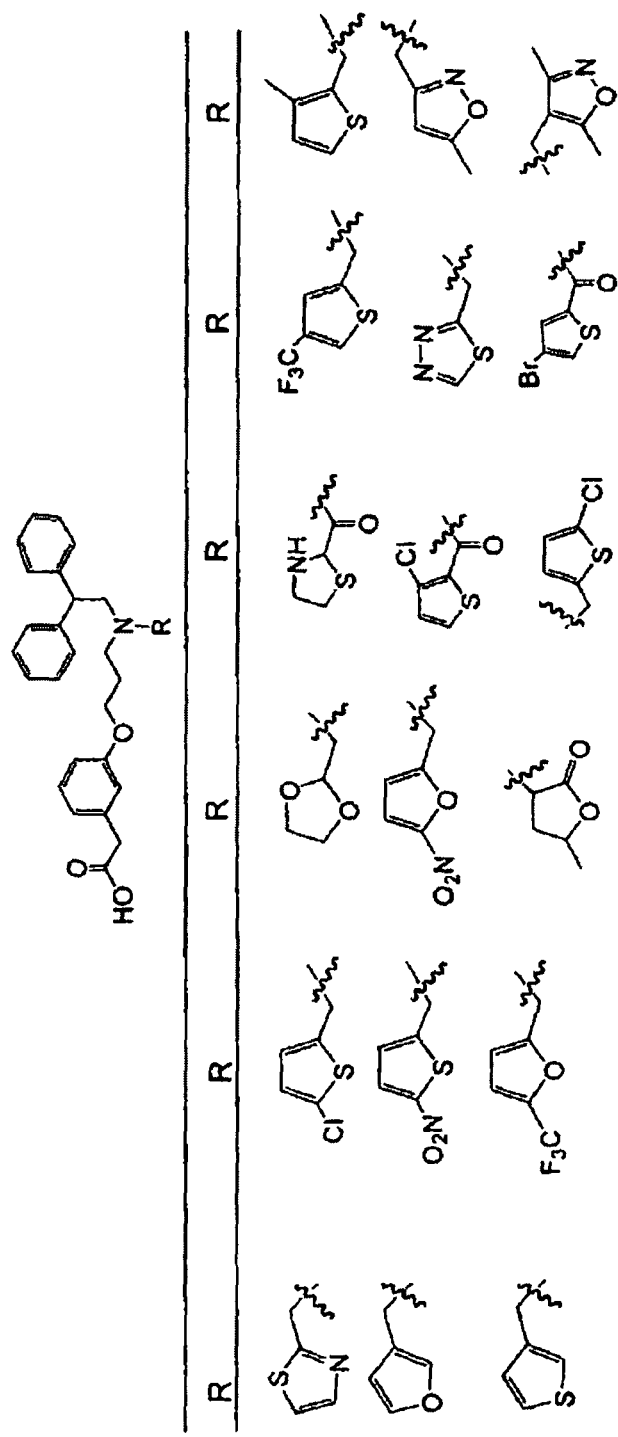
FIG. 5 shows samples compounds stemming from the {3-(3-[(2,2-diphenyl-ethylamino)-propoxy]-phenyl}-acetic acid (5) compound library.

A total of 96 target compounds will be produced via this method by incorporating a maximum of 96 different R groups into this position. Examples of compounds from the final target library are illustrated in FIG. 5.

Example 6

Chemical Synthesis of Other Compounds or Ligands

Organic reagents were purchased from commercial suppliers unless otherwise noted and were used without further purification. All solvents were analytical or reagent grade. All reactions were carried out in flame-dried glassware under argon or nitrogen. Melting points were determined and reported automatically by an optoelectronic sensor in open capillary tubes and were uncorrected. $^1$H NMR and $^{13}$C NMR spectra were measured at 500 MHz and 125 MHz respectively, and using $CDCl_3$ or $CD_3OD$ as the solvents and tetramethylsilane ($Me_4Si$) as the internal standard. Liquid column chromatography was carried out under moderate pressure by using columns of an appropriate size packed and eluted with appropriate eluents. All reactions were monitored by TLC on precoated plates (silica gel HLF). TLC spots were visualized either by exposure to iodine vapors or by irradiation with UV light. Organic solvents were removed in vacuum by rotary evaporator. Elemental analyses were performed by Desert Analytics, Tucson, Ariz.

(3-Hydroxy-phenyl)-acetic acid methyl ester (1). To a solution of 3-hydroxyphenyl acetic acid, (5.0 g, 0.033 mol) in methanol (100 mL) was added concentrated sulfuric acid (1 mL) and the reaction mixture stirred at room temperature for 12 hours. After concentration to remove methanol, the crude oil was dissolved in ethyl acetate (75 mL), washed with water (50 ml), saturated aqueous NaHCO3 (50 mL), and brine (50 ml). The organic layer was dried over $Na_2SO_4$, and concentrated to give the methyl ester (1) as an oil (5.28 g) in 96% yield, which was used without further purification. $^1$H NMR ($CDCl_3$) δ 7.17 (t, 1H), 6.81 (m, 3H), 6.48 (s, 1H), 3.69 (s, 3H), 3.57 (s, 2H). $^{13}$C NMR ($CDCl_3$) δ 169.9, 153.3, 132.3, 126.9, 118.4, 111.5, 57.8, 38.4.

[3-(3-Bromo-propoxy)-phenyl]-acetic acid methyl ester (2). A solution of 3-hydroxyphenyl acetic acid methyl ester (1) (5.28 g, 0.032 mol), 3-bromo-1-propanol (6.95 g, 0.05 mol), and $Ph_3P$ in $CH_2Cl_2$ (100 mL) was treated with diisopropyl azodicarboxylate (6.67 g, 0.033 mol) dropwise. The reaction mixture stirred at room temperature for 12 hours and was concentrated to an oil, which was purified by flash chromatography (gradient elution, 9:1 to 7:3 Hexanes/EtOAc to give the desired product as oil 7.90 g in 86% yield. $^1$H NMR ($CDCl_3$) δ 7.25 (t, 1H), 6.88 (d, 1H), 6.84 (m, 2H), 4.11 (t, 2H), 3.70 (s, 3H), 3.61 (m, 4H), 2.34 (m, 2H). $^{13}$C NMR ($CDCl_3$) δ 169.0, 155.9, 132.5, 126.7, 119.0, 112.7, 110.3, 62.3, 49.2, 38.3, 29.5, 27.1.

{3-[3-(2,2-Diphenyl-ethylamino)-propoxy]-phenyl}-acetic acid methyl ester (3). A solution of [3-(3-bromo-propoxy)-phenyl]-acetic acid methyl ester (2) (2.0 g, 0.007 mol) and 2,2-diphenylethylamine (2.5 g, 0.013 mol) in DMSO (5 mL) was stirred at room temperature for 18 hours. The reaction mixture was diluted with water (30 mL) and extracted with EtOAc (3×25 mL). The combined organic extracts were washed with brine (15 mL), dried over $Na_2SO_4$, concentrated to an oil, which was purified by flash chromatography (9:1 $CH_2Cl_2$/MeOH) to give the desired product as oil 2.72 g in 96% yield. $^1$H NMR ($CDCl_3$) δ 7.24 (m, 7H), 7.19 (t, 3H), 6.85 (d, 1H), 6.74 (s, 1H), 6.72 (d, 2H), 5.26 (s, 1H), 4.22 (t, 1H), 3.96 (t, 2H), 3.68 (s, 3H), 3.57 (d, 2H), 3.26 (d, 2H), 2.84 (t, 2H), 1.92 (m, 2H). $^{13}$C NMR ($CDCl_3$) δ 173.3, 160.5, 144.4, 136.7, 130.9, 130.1, 129.5, 129.4, 127.9, 122.9, 116.9, 114.6, 67.6, 56.0, 53.5, 52.6, 48.3, 42.6, 31.0.

(3-{3-[(2,2-Diphenyl-ethyl)-(2-fluoro-3-trifluoromethyl-benzyl)-amino]-propoxy}-phenyl)-acetic acid methyl ester (4a). To a solution of {3-[3-(2,2-diphenyl-ethylamino)-propoxy]-phenyl}-acetic acid methyl ester (3) (0.7 g, 0.002 mol) in DMF (10 mL), was added 2-fluoro-3-(trifluoromethyl) benzyl bromide (0.5 g, 0.002 mol) and powdered potassium carbonate (1.93 g, 0.014 mol), the reaction mixture was heated and stirred at 45° C. for 18 hours. After cooling, the reaction mixture was diluted with water (30 mL) and extracted with EtOAc (3×25 mL). The combined organic extracts were washed with brine (15 mL), dried over $Na_2SO_4$, concentrated to an oil, which was purified by flash chromatography (8:2 Hexanes/EtOAc) to give the desired product as oil 0.84 g in 72% yield. $^1$H NMR ($CDCl_3$) δ 7.35 (t, 1H), 7.17 (m, 12H), 6.85 (t, 2H), 6.63 (s, 1H), 6.59 (t, 1H), 4.16 (t, 1H), 3.69 (s, 3H), 3.68 (s, 2H), 3.63 (t, 2H), 3.57 (d, 2H), 3.10 (d, 2H), 2.67 (t, 2H), 1.82 (t, 2H). $^{13}$C NMR ($CDCl_3$) δ 173.4, 160.4, 144.8, 136.6, 130.8, 130.8, 129.7, 129.6, 129.4, 127.7, 126.8, 124.9, 123.1, 122.8, 116.8, 114.5, 66.3, 61.4, 53.5, 52.4, 51.8, 51.1, 42.7, 28.3.

(3-{3-[(2,2-Diphenyl-ethyl)-(2,3-difluoro-benzyl)-amino]-propoxy}-phenyl)-acetic acid methyl ester (4b). To a solution of {3-[3-(2,2-diphenyl-ethylamino)-propoxy]-phenyl}-acetic acid methyl ester (3) (0.7 g, 0.002 mol) in DMF (10 mL), was added 2-fluoro-3-(trifluoromethyl)benzyl bromide (0.5 g, 0.002 mol) and powdered potassium carbonate (1.93 g, 0.014 mol), the reaction mixture was heated and stirred at 45° C. for 18 hours. After cooling, the reaction mixture was diluted with water (30 mL) and extracted with EtOAc (3×25 mL). The combined organic extracts were washed with brine (15 mL), dried over $Na_2SO4$, concentrated to an oil, which was purified by flash chromatography (8:2 Hexanes/EtOAc) to give the desired product as oil 0.93 g in 88% yield. $^1$H NMR ($CDCl_3$) δ 7.18 (s, 1H), 7.17 (m, 10H), 6.94 (t, 1H), 6.84 (d, 1H), 6.76 (t, 2H), 6.65 (m 2H), 4.16 (t, 1H), 3.68 (s, 3H), 3.67 (s, 2H), 3.56 (s, 2H), 3.07 (d, 2H), 2.66 (t, 2H), 1.81 (t, 2H), 1.54 (t, 2H). $^{13}$C NMR ($CDCl_3$) δ 173.4, 160.5, 149.6, 144.8, 136.6, 131.0, 130.8, 130.0, 129.6, 129.4, 127.6, 127.3, 124.9, 122.2, 122.7, 116.9, 114.5, 66.6, 61.2, 53.5, 52.6, 51.7, 51.1, 42.7, 28.3.

(3-{3-[(2,2-Diphenyl-ethyl)-(3-trifluoromethoxy-benzyl)-amino]-propoxy}-phenyl)-acetic acid methyl ester (4c). To a solution of {3-[3-(2,2-diphenyl-ethylamino)-propoxy]-phenyl}-acetic acid methyl ester (3) (0.5 g, 0.0012 mol) in DMF (10 mL), was added 3-(trifluoromethoxy)benzyl bromide (0.47 g, 0.0018 mol) and powdered potassium carbonate (1.16 g, 0.0084 mol), the reaction mixture was heated and stirred at 45° C. for 18 hours. After cooling, the reaction mixture was diluted with water (30 mL) and extracted with EtOAc (3×25 mL). The combined organic extracts were washed with brine (15 mL), dried over $Na_2SO4$, concentrated to an oil, which was purified by flash chromatography (9:1 Hexanes/EtOAc) to give the desired product as oil 0.61 g in 88% yield. $^1$H NMR ($CDCl_3$) δ 7.20 (s, 1H), 7.19 (m, 11H), 7.04 (s, 1H), 7.01 (t, 2H), 6.88 (d, 1H), 6.69 (m 2H), 4.20 (t, 1H), 3.70 (s, 3H), 3.63 (s, 2H), 3.59 (s, 2H), 3.13 (d, 2H), 2.67 (t, 2H), 1.84 (t, 2H); $^{13}$C NMR ($CDCl_3$) δ 173.4, 160.5, 149.6, 144.8, 136.7, 131.0, 130.9, 130.0, 129.8, 129.7, 129.6, 128.4, 127.8, 122.8, 122.7, 122.5, 120.6, 116.9, 114.5, 66.8, 61.3, 60.1, 53.4, 51.9, 51.2, 42.7, 28.2.

(3-{3-[(2,2-Diphenyl-ethyl)-(3-methoxy-benzyl)-amino]-propoxy}-phenyl)-acetic acid methyl ester (4d). To a solution of {3-[3-(2,2-diphenyl-ethylamino)-propoxy]-phenyl}-acetic acid methyl ester (3) (0.74 g, 0.002 mol) in DMF (10 mL), was added 3-methoxybenzyl bromide (0.47 g, 0.0023 mol) and powdered potassium carbonate (1.93 g, 0.014 mol), the reaction mixture was heated and stirred at 45° C. for 18 hours. After cooling, the reaction mixture was diluted with water (30 mL) and extracted with EtOAc (3×25 mL). The combined organic extracts were washed with brine (15 mL), dried over Na$_2$SO4, concentrated to an oil, which was purified by flash chromatography (8:2 Hexanes/EtOAc) to give the desired product as oil 0.81 g in 77% yield. $^1$H NMR (CDCl$_3$) δ 7.19 (s, 1H), 7.17 (m, 11H), 7.09 (t, 1H), 6.83 (d, 1H), 6.72 (t, 2H), 6.59 (m 2H), 4.19 (t, 1H), 3.72 (s, 6H), 3.61 (s, 4H), 3.55 (d, 2H), 3.07 (d, 2H), 2.62 (t, 2H), 1.82 (t, 2H); $^{13}$C NMR (CDCl$_3$) δ 173.4, 160.9, 160.6, 144.9, 142.8, 136.6, 130.8, 130.3, 129.9, 129.7, 129.6, 127.6, 122.7, 122.6, 116.9, 115.2, 114.5, 114.3, 67.0, 61.2, 60.6, 56.4, 51.9, 51.2, 42.7, 28.2.

(3-{3-[(2,2-Diphenyl-ethyl)-(3,5-bis(trifluoromethyl)-benzyl)-amino]-propoxy}-phenyl)-acetic acid methyl ester (4e). To a solution of {3-[3-(2,2-diphenyl-ethylamino)-propoxy]-phenyl}-acetic acid methyl ester (3) (0.50 g, 0.0012 mol) in DMF (10 mL), was added 3,5-bis (trifluoromethyl)-benzyl bromide (0.50 g, 0.0016 mol) and powdered potassium carbonate (1.55 g, 0.011 mol), the reaction mixture was heated and stirred at 45° C. for 18 hours. After cooling, the reaction mixture was diluted with water (30 mL) and extracted with EtOAc (3×25 mL). The combined organic extracts were washed with brine (15 mL), dried over Na$_2$SO4, concentrated to an oil, which was purified by flash chromatography (8:2 Hexanes/EtOAc) to give the desired product as oil 0.57 g in 77% yield. $^1$H NMR (CDCl$_3$) δ 7.61 (s, 1H), 7.50 (s, 2H), 7.24 (m, 12H), 6.83 (d, 1H), 6.62 (s, 1H), 6.59 (dd 1H), 4.19 (t, 1H), 3.68 (s, 2H), 3.67 (s, 3H), 3.60 (t, 2H), 3.56 (d, 2H), 3.14 (d, 2H), 2.64 (t, 2H), 1.83 (t, 2H); $^{13}$C NMR (CDCl$_3$) δ 173.3, 160.3, 144.3, 136.7, 132.8, 130.9, 130.1, 129.9, 129.7, 129.5, 128.0, 125.9, 123.7, 122.9, 122.3, 116.2, 114.5, 114.4, 66.6, 61.1, 59.7, 53.4, 52.1, 51.3, 42.6, 28.1.

(3-{3-[(2,2-Diphenyl-ethyl)-(3-iodo-benzyl)-amino]-propoxy}-phenyl)-acetic acid methyl ester (4f). To a solution of {3-[3-(2,2-diphenyl-ethylamino)-propoxy]-phenyl}-acetic acid methyl ester (3) (0.50 g, 0.0012 mol) in DMF (10 mL), was added 3-iodobenzyl bromide (0.36 g, 0.0012 mol) and powdered potassium carbonate (1.16 g, 0.0084 mol), the reaction mixture was heated and stirred at 45° C. for 18 hours. After cooling, the reaction mixture was diluted with water (30 mL) and extracted with EtOAc (3×25 mL). The combined organic extracts were washed with brine (15 mL), dried over Na$_2$SO4, concentrated to an oil, which was purified by flash chromatography (8:2 Hexanes/EtOAc) to give the desired product as oil 0.6 g in 81% yield. $^1$H NMR (CDCl$_3$) δ 7.48 (d, 1H), 7.42 (s, 1H), 7.24 (m, 5H), 7.15 (m, 6H), 6.99 (d, 1H), 6.86 (m, 2H), 6.65 (s, 1H), 6.63 (dd, 1H), 4.16 (t, 1H), 3.67 (s, 3H), 3.60 (t, 2H), 3.58 (s, 2H), 3.52 (s, 2H), 3.05 (d, 2H), 2.61 (t, 2H), 1.81 (t, 2H); $^{13}$C NMR (CDCl$_3$) δ 173.4, 160.5, 144.7, 143.7, 139.2, 137.3, 136.6, 131.2, 130.9, 129.8, 129.7, 129.6, 129.4, 127.8, 122.7, 116.9, 114.5, 95.6, 66.9, 61.1, 59.9, 53.5, 51.8, 51.1, 42.7, 28.2.

(3-{3-[(2,2-Diphenyl-ethyl)-(3-trifluoromethyl-benzyl)-amino]-propoxy}-phenyl)-acetic acid methyl ester (4g). To a solution of {3-[3-(2,2-diphenyl-ethylamino)-propoxy]-phenyl}-acetic acid methyl ester (3) (0.40 g, 0.001 mol) in DMF (10 mL), was added 3-trifluoromethylbenzyl bromide (0.24 g, 0.001 mol) and powdered potassium carbonate (0.96 g, 0.007 mol), the reaction mixture was heated and stirred at 45° C. for 18 hours. After cooling, the reaction mixture was diluted with water (30 mL) and extracted with EtOAc (3×25 mL). The combined organic extracts were washed with brine (15 mL), dried over Na$_2$SO4, concentrated to an oil, which was purified by flash chromatography (8:2 Hexanes/EtOAc) to give the desired product as oil 0.43 g in 77% yield. $^1$H NMR (CDCl$_3$) δ 7.40 (d, 1H), 7.37 (s, 1H), 7.24 (m, 7H), 7.19 (m, 6H), 6.83 (d, 1H), 6.62 (s, 1H), 6.59 (dd, 1H), 4.16 (t, 1H), 3.67 (s, 3H), 3.63 (s, 2H), 3.58 (t, 2H), 3.55 (s, 2H), 3.08 (d, 2H), 2.61 (t, 2H), 1.79 (t, 2H); $^{13}$C NMR (CDCl$_3$) δ 173.4, 160.4, 144.7, 143.7, 142.2, 136.6, 133.8, 133.5, 131.9, 130.8, 130.2, 129.9, 129.8, 127.8, 126.8, 125.1, 125.0, 122.7, 116.8, 115.7, 114.5, 66.8, 61.1, 60.2, 53.5, 51.8, 42.6, 28.2.

(3-{3-[(2,2-Diphenyl-ethyl)-(3-chloro-benzyl)-amino]-propoxy}-phenyl)-acetic acid methyl ester (4h). To a solution of {3-[3-(2,2-diphenyl-ethylamino)-propoxy]-phenyl}-acetic acid methyl ester (3) (0.34 g, 0.0008 mol) in DMF (10 mL), was added 3-chlorobenzyl bromide (0.25 g, 0.0012 mol) and powdered potassium carbonate (0.77 g, 0.0056 mol), the reaction mixture was heated and stirred at 45° C. for 18 hours. After cooling, the reaction mixture was diluted with water (30 mL) and extracted with EtOAc (3×20 mL). The combined organic extracts were washed with brine (15 mL), dried over Na$_2$SO4, concentrated to an oil, which was purified by flash chromatography (8:2 Hexanes/EtOAc) to give the desired product as oil 0.33 g in 77% yield. $^1$H NMR (CDCl$_3$) δ 7.23 (d, 2H), 7.18 (m, 4H), 7.14 (m, 6H), 6.91 (d, 2H), 6.83 (d, 1H), 6.82 (d, 1H), 6.65 (s, 1H), 6.63 (d, 1H), 4.16 (t, 1H), 3.67 (s, 3H), 3.63 (t, 2H), 3.57 (s, 2H), 3.55 (s, 2H), 3.05 (d, 2H), 2.63 (t, 2H), 1.80 (t, 2H); $^{13}$C NMR (CDCl$_3$) δ 173.3, 160.5, 144.7, 143.3, 136.6, 135.3, 130.8, 130.7, 130.3, 129.7, 129.6, 128.4, 128.3, 127.7, 122.7, 116.9, 114.5, 66.9, 61.1, 60.1, 53.5, 51.8, 51.1, 42.7, 28.2.

(3-{3-[(2,2-Diphenyl-ethyl)-(3,5-di-tert-butyl-benzyl)-amino]-propoxy}-phenyl)-acetic acid methyl ester (4l). To a solution of {3-[3-(2,2-diphenyl-ethylamino)-propoxy]-phenyl}-acetic acid methyl ester (3) (0.40 g, 0.001 mol) in DMF (10 mL), was added 3,5-di-tert-butyl-benzyl bromide (0.30 g, 0.0011 mol) and powdered potassium carbonate (0.96 g, 0.007 mol), the reaction mixture was heated and stirred at 45° C. for 18 hours. After cooling, the reaction mixture was diluted with water (30 mL) and extracted with EtOAc (3×25 mL). The combined organic extracts were washed with brine (15 mL), dried over Na$_2$SO4, concentrated to an oil, which was purified by flash chromatography (9:1 Hexanes/EtOAc) to give the desired product as oil 0.56 g in 92% yield. $^1$H NMR (CDCl$_3$) δ 7.19 (m, 10H), 7.12 (t, 2H), 7.01 (d, 2H), 6.82 (d, 1H), 6.63 (s, 1H), 6.59 (d, 1H), 4.17 (t, 1H), 3.67 (s, 3H), 3.62 (s, 2H), 3.57 (t, 2H), 3.55 (s, 2H), 3.10 (d, 2H), 2.58 (t, 2H), 1.77 (t, 2H), 1.26 (s, 18H). $^{13}$C NMR (CDCl$_3$) δ 173.3, 160.6, 151.8, 145.1, 140.1, 136.5, 130.8, 129.8, 129.7, 129.6, 129.5, 127.6, 124.5, 122.6, 122.1, 117.0, 114.6, 67.3, 61.3, 53.4, 52.3, 51.2, 51.1, 42.7, 36.1, 32.9, 28.2.

(3-{3-[(2,2-Diphenyl-ethyl)-(3,5-dimethoxy-benzyl)-amino]-propoxy}-phenyl)-acetic acid methyl ester (4j). To a solution of {3-[3-(2,2-diphenyl-ethylamino)-propoxy]-phenyl}-acetic acid methyl ester (3) (0.30 g, 0.00074 mol) in DMF (10 mL), was added 3,5-dimethoxy-benzyl bromide (0.23 g, 0.0011 mol) and powdered potassium carbonate (0.96 g, 0.007 mol), the reaction mixture was heated and stirred at 45° C. for 18 hours. After cooling, the reaction mixture was diluted with water (30 mL) and extracted with EtOAc (3×25 mL). The combined organic extracts were washed with brine (15 mL), dried over Na$_2$SO4, concentrated to an oil, which was purified by flash chromatography (8:2 Hexanes/EtOAc) to give the desired product as oil 0.30 g in 92% yield. $^1$H NMR (CDCl$_3$) δ 7.20 (m, 9H), 7.11 (t, 2H), 6.83 (d, 1H), 6.64 (s, 1H), 6.62 (d, 1H), 6.26 (s, 3H), 4.18 (t, 1H), 3.67 (s, 3H), 3.63 (s, 6H), 3.61 (s, 2H), 3.56 (s, 2H), 3.54 (t, 2H), 3.08 (d, 2H), 2.60 (t, 2H), 1.79 (t, 2H). $^{13}$C NMR (CDCl$_3$) δ 173.3, 161.9, 160.5, 144.9, 143.8, 136.6, 130.8, 129.7, 129.6, 127.6, 122.7, 116.9, 114.5, 107.8, 100.6, 67.1, 61.2, 60.8, 56.6, 53.4, 52.0, 51.2, 42.7, 28.2.

(3-{3-[(2,2-Diphenyl-ethyl)-(2-fluoro-3-trifluoromethyl-benzyl)-amino]-propoxy}-phenyl)-acetic acid (DY136). A solution of (3-{3-[(2,2-Diphenyl-ethyl)-(2-fluoro-3-trifluoromethyl-benzyl)-amino]-propoxy}-phenyl)-acetic acid methyl ester (4a) (0.84 g, 0.0014 mol) in methanol (7.5 mL) was treated with 2N NaOH (5.0 ml) and the mixture stirred overnight at ambient temperature. After concentration to dryness, the residue was diluted with EtOAc (25 mL), water (10 mL) was added, and the solution acidified to pH 2 with concentrated hydrochloric acid, then extracted into EtOAc (3×20 mL). The combined organic extracts were dried over Na$_2$SO$_4$, and then concentrated in vacuo to provide the carboxylic acid as waxy oil. Solidification of the waxy oil from 9:1 ether/pet ether gave white solid (5a) 0.67 g in 85% yield, mp: 181.4° C. $^1$H NMR (CD$_3$OD) δ 7.84 (d, 2H), 7.46 (m, 11H), 6.88 (d, 2H), 6.68 (d, 2H), 4.67 (s, 2H), 4.64 (t, 1H), 4.11 (s, 2H), 3.99 (d, 2H), 3.54 (s, 2H), 3.45 (d, 2H), 2.27 (t, 2H); $^{13}$C NMR (CD$_3$OD) δ 175.3, 159.5, 141.3, 139.1, 137.6, 131.1, 130.6, 130.5, 128.9, 126.8, 126.7, 123.6, 116.9, 114.0, 66.4, 59.0, 53.9, 52.0, 41.5, 23.5. Anal. Calcd for C$_{33}$H$_{31}$F$_4$NO$_3$.2H$_2$O: C, 65.87; H, 5.19; N, 2.33; F, 12.63. Found: C, 65.80; H, 5.34; N, 2.08; F, 12.51.

(3-{3-[(2,2-Diphenyl-ethyl)-(2,3-difluoro-benzyl)-amino]-propoxy}-phenyl)-acetic acid (DY137). A solution of (3-{3-[(2,2-Diphenyl-ethyl)-(2,3-difluoro-benzyl)-amino]-propoxy}-phenyl)-acetic acid methyl ester (4b). (0.83 g, 0.0016 mol) in methanol (7.5 mL) was treated with 2N NaOH (5.0 ml) and the mixture stirred overnight at ambient temperature. After concentration to dryness, the residue was dissolved in EtOAc (25 mL) and water was added (10 mL), the solution acidified to pH 3 with concentrated hydrochloric acid, then extracted into EtOAc (3×20 mL). The combined organic extracts were dried over Na$_2$SO$_4$, and then concentrated in vacuo to provide the carboxylic acid as waxy oil. Solidification of the waxy oil from EtOAc gave white solid (5a) 0.73 g in 88% yield, mp: 148.4° C. $^1$H NMR (CD$_3$OD) δ 7.18 (m, 1H), 6.99 (m, 1H), 6.81 (d, 2H), 6.76 (m, 1H), 6.72 (s, 1H), 6.55 (d, 1H), 4.17 (t, 1H), 3.67 (s, 2H), 3.55 (s, 2H), 3.54 (d, 2H), 3.07 (d, 2H), 2.62 (t, 2H), 1.77 (t, 2H); $^{13}$C NMR (CD$_3$OD) δ 175.6, 160.5, 152.7, 151.5, 149.5, 149.4, 145.1, 137.3, 130.3, 130.1, 129.1, 127.6, 125.0, 124.9, 122.4, 129.3, 116.6, 114.1, 66.0, 60.9, 52.2, 51.3, 51.1, 42.2, 28.0. Anal. Calcd for C$_{32}$H$_{31}$F$_2$NO$_3$.2$_{1/2}$H$_2$O: C, 68.55; H, 5.57; N, 2.50; F, 6.77. Found: C, 68.62; H, 5.27; N, 2.28; F, 6.52.

(3-{3-[(2,2-Diphenyl-ethyl)-(3-trifluoromethoxy-benzyl)-amino]-propoxy}-phenyl)-acetic acid (DY138). A solution of (3-{3-[(2,2-Diphenyl-ethyl)-(3-trifluoromethoxy-benzyl)-amino]-propoxy}-phenyl)-acetic acid methyl ester (4c). (0.58 g, 0.001 mol) in methanol (7.5 mL) was treated with 2N NaOH (5.0 ml) and the mixture stirred overnight at ambient temperature. After concentration to dryness, the residue was dissolved in EtOAc (25 mL) and water was added (10 mL), the solution acidified to pH 3 with concentrated hydrochloric acid, then extracted into EtOAc (3×20 mL). The combined organic extracts were dried over Na$_2$SO$_4$, and then concentrated in vacuo to provide the carboxylic acid as waxy oil (5c) 0.5 g in 89% yield. $^1$H NMR (CD$_3$OD) δ 7.22 (m, 12H), 7.05 (d, 1H), 7.01 (d, 1H), 6.98 (s, 1H), 6.63 (d, 1H), 6.61 (s, 1H), 6.57 (d, 1H), 4.22 (t, 1H), 3.61 (s, 2H), 3.58 (t, 2H), 3.54 (s, 2H), 3.11 (d, 2H), 2.63 (t, 2H), 1.79 (t, 2H); $^{13}$C NMR (CD$_3$OD) δ 175.7, 160.4, 150.4, 145.0, 143.9, 137.3, 130.6, 130.5, 130.2, 129.5, 129.2, 128.6, 127.3, 122.4, 120.9, 120.3, 116.5, 114.1, 66.3, 60.9, 59.6, 58.3, 51.6, 51.1, 42.2, 27.9. Anal. Calcd for C$_{33}$H$_{32}$F$_3$NO$_4$: C, 70.32; H, 5.72; N, 2.49; F, 10.11. Found: C, 70.05; H, 5.93; N, 2.58; F, 9.84.

(3-{3-[(2,2-Diphenyl-ethyl)-(3-methoxy-benzyl)-amino]-propoxy}-phenyl)-acetic acid (DY139). A solution of (3-{3-[(2,2-Diphenyl-ethyl)-(3-methoxy-benzyl)-amino]-propoxy}-phenyl)-acetic acid methyl ester (4d). (0.2 g, 0.00038 mol) in methanol (5 mL) was treated with 2N NaOH (2.5 mL) and the mixture stirred overnight at ambient temperature. After concentration to dryness, the residue was dissolved in EtOAc (25 mL) and water was added (10 mL), the solution acidified to pH 3 with concentrated hydrochloric acid, then extracted into EtOAc (3×20 mL). The combined organic extracts were dried over Na$_2$SO$_4$, and then concentrated in vacuo to provide the carboxylic acid as waxy oil. Solidification of the waxy oil from pet. ether gave white solid (5d) 0.16 g in 84% yield, mp: 42.1° C. $^1$H NMR (CD$_3$OD) δ 7.39 (t, 1H), 7.28 (m, 111H), 7.07 (d, 1H), 7.03 (t, 2H), 6.89 (d, 1H), 6.69 (s, 1H), 6.67 (s, 1H), 4.46 (t, 1H), 4.40 (s, 1H), 4.09 (d, 2H), 3.97 (s, 2H), 3.76 (s, 3H), 3.62 (t, 2H), 3.57 (s, 1H), 3.30 (t, 2H), 2.24 (t, 1H), 1.99 (d, 1H); $^{13}$C NMR (CD$_3$OD) δ 175.3, 161.9, 159.6, 141.4, 137.6, 131.7, 130.6, 130.5, 130.3, 128.8, 128.7, 124.2, 123.6, 117.7, 117.0, 116.3, 116.7, 114.0, 105.2, 66.7, 59.6, 58.3, 55.9, 53.9, 41.9, 24.7. Anal. Calcd for C$_{33}$H$_{35}$NO$_4$.2.5H$_2$O: C, 71.45; H, 6.36; N, 2.52. Found: C, 71.16; H, 6.83; N, 2.43.

(3-{3-[(2,2-Diphenyl-ethyl)-(3,5-bis(trifluoromethyl)-benzyl)-amino]-propoxy}-phenyl)-acetic acid (DY140). A solution of (3-{3-[(2,2-Diphenyl-ethyl)-(3,5-bis(trifluoromethyl)-benzyl)-amino]-propoxy}-phenyl)-acetic acid methyl ester (4e). (0.57 g, 0.001 mol) in methanol (7.5 mL) was treated with 2N NaOH (5 mL) and the mixture stirred overnight at ambient temperature. After concentration to dryness, the residue was dissolved in EtOAc (25 mL) and water was added (10 mL), the solution acidified to pH 3 with concentrated hydrochloric acid, then extracted into EtOAc (3×20 mL). The combined organic extracts were dried over Na$_2$SO$_4$, and then concentrated in vacuo to provide the carboxylic acid as waxy oil, which was purified by flash chromatography (9:1 CH$_2$Cl$_2$/MeOH) to give the desired product as oil 0.49 g in 79% yield. $^1$H NMR (CD$_3$OD) δ 7.70 (s, 1H), 7.66 (s, 2H), 7.23 (m, 8H), 7.14 (m, 3H), 6.82 (d, 1H), 6.58 (s, 1H), 6.54 (dd, 1H), 4.26 (t, 1H), 3.77 (s, 2H), 3.56 (t, 2H), 3.52 (s, 2H), 3.16 (d, 2H), 2.64 (t, 2H), 1.82 (t, 2H); $^{13}$C NMR (CD$_3$OD) δ 175.6, 160.3, 145.3, 144.9, 137.3, 132.4, 130.3, 130.2, 129.4, 129.3, 127.4, 122.5, 121.5, 116.4, 113.9, 66.3, 61.0, 59.1, 51.8, 51.3, 42.1, 27.9. Anal. Calcd for C$_{34}$H$_{31}$F$_6$NO$_3$: C, 66.34; H, 5.08; N, 2.08; F, 18.52. Found: C, 66.10; H, 5.07; N, 2.21; F, 18.69.

(3-{3-[(2,2-Diphenyl-ethyl)-(3-iodo-benzyl)-amino]-propoxy}-phenyl)-acetic acid (DY141). A solution of (3-{3-[(2,2-Diphenyl-ethyl)-(3-iodo-benzyl)-amino]-propoxy}-phenyl)-acetic acid methyl ester (4f). (0.5 g, 0.0008 mol) in methanol (7.5 mL) was treated with 2N NaOH (5 mL) and the mixture stirred overnight at ambient temperature. After concentration to dryness, the residue was dissolved in EtOAc (25 mL) and water was added (10 mL), the solution acidified to pH 3 with concentrated hydrochloric acid, then extracted into EtOAc (3×20 mL). The combined organic extracts were dried over Na$_2$SO$_4$, and then concentrated in vacuo to provide the carboxylic acid as waxy oil, which was purified by flash chromatography (9:1 CH$_2$Cl$_2$/MeOH) to give the desired product as oil 0.32 g in 67% yield. $^1$H NMR (CD$_3$OD) δ 7.92 (s, 1H), 7.53 (d, 2H), 7.27 (m, 8H), 7.19 (t, 2H), 6.93 (t, 1H), 6.88 (d, 1H), 6.67 (s, 1H), 6.64 (d, 1H), 4.25 (t, 1H), 3.70 (s, 2H), 3.65 (t, 2H), 3.58 (s, 2H), 3.16 (d, 2H), 2.69 (t, 2H), 1.86 (t, 2H); $^{13}$C NMR (CD$_3$OD) δ 175.7, 160.4, 144.8, 144.7, 143.2, 139.3, 137.3, 137.2, 137.1, 131.0, 130.9, 130.4, 129.5, 129.3, 127.4. 122.5, 122.4, 116.6, 114.3, 94.9, 66.5, 60.7, 59.5, 51.7, 50.9, 42.2, 27.7. Anal. Calcd for $C_{32}H_{32}INO_3 \cdot H_2O$: C, 61.62; H, 5.17; I, 20.34; N, 2.25. Found: C, 61.70; H, 5.06; I, 20.68; N, 2.74.

(3-{3-[(2,2-Diphenyl-ethyl)-(3-trifluoromethyl-benzyl)-amino]-propoxy}-phenyl)-acetic acid (DY142). A solution of (3-{3-[(2,2-Diphenyl-ethyl)-(3-trifluoromethyl-benzyl)-amino]-propoxy}-phenyl)-acetic acid methyl ester (4g). (0.37 g, 0.0007 mol) in methanol (7.5 mL) was treated with 2N NaOH (5 mL) and the mixture stirred overnight at ambient temperature. After concentration to dryness, the residue was dissolved in EtOAc (25 mL) and water was added (10 mL), the solution acidified to pH 3 with concentrated hydrochloric acid, then extracted into EtOAc (3×20 mL). The combined organic extracts were dried over $Na_2SO_4$, and then concentrated in vacuo to provide the carboxylic acid as waxy oil, which was purified by flash chromatography (9:1 $CH_2Cl_2$/MeOH) to give the desired product as oil 0.33 g in 87% yield. $^1H$ NMR ($CD_3OD$) δ 7.38 (d, 2H), 7.26 (t, 1H), 7.21 (m, 8H), 7.13 (t, 4H), 6.82 (d, 1H), 6.59 (s, 1H), 6.53 (d, 1H), 4.21 (t, 1H), 3.68 (s, 2H), 3.55 (t, 2H), 3.52 (s, 2H), 3.10 (d, 2H), 2.61 (t, 2H), 1.79 (t, 2H); $^{13}C$ NMR ($CD_3OD$) δ 173.7, 160.4, 145.1, 142.7, 139.3, 133.7, 130.2, 129.8, 127.3, 126.5, 124.6, 122.4, 116.5, 113.9, 66.3, 60.9, 59.7, 51.5, 51.2, 42.6, 27.9. Anal. Calcd for $C_{33}H_{32}F_3NO_3$: C, 72.38; H, 5.89; N, 2.56; F, 10.41. Found: C, 72.29; H, 6.09; N, 2.96; F, 10.08.

(3-{3-[(2,2-Diphenyl-ethyl)-(3-chloro-benzyl)-amino]-propoxy}-phenyl)-acetic acid (DY143). A solution of (3-{3-[(2,2-Diphenyl-ethyl)-(3-chloro-benzyl)-amino]-propoxy}-phenyl)-acetic acid methyl ester (4h). (0.15 g, 0.0003 mol) in methanol (3 mL) was treated with 2N NaOH (2 mL) and the mixture stirred overnight at ambient temperature. After concentration to dryness, the residue was dissolved in EtOAc (15 mL) and water was added (5 mL), the solution acidified to pH 3 with concentrated hydrochloric acid, then extracted into EtOAc (3×20 mL). The combined organic extracts were dried over $Na_2SO_4$, and then concentrated in vacuo to provide the carboxylic acid as waxy oil, which was purified by flash chromatography (9:1 $CH_2Cl_2$/MeOH) to give the desired product as oil 0.11 g in 73% yield. $^1H$ NMR ($CD_3OD$) δ 7.22 (m, 8H), 7.18 (t, 4H), 7.16 (s, 1H), 7.12 (t, 1H), 7.04 (d, 1H), 6.88 (d, 1H), 6.67 (s, 1H), 6.63 (d, 1H), 4.26 (t, 1H), 3.67 (s, 2H), 3.63 (t, 2H), 3.59 (s, 2H), 3.14 (d, 2H), 2.68 (t, 2H), 1.86 (t, 2H); $^{13}C$ NMR ($CD_3OD$) δ 175.8, 160.5, 145.0, 143.3, 137.4, 135.0, 136.6, 130.2, 130.1, 129.4, 129.3, 128.4, 128.0, 127.3, 122.4, 116.5, 114.1, 66.4, 60.9, 59.7, 51.5, 51.1, 42.3, 27.9. Anal. Calcd for $C_{23}H_{32}ClNO_3 \cdot H_2O$: C, 72.23; H, 6.06; N, 2.63; Cl, 6.67. Found: C, 72.53; H, 6.09; N, 2.96; Cl, 7.08.

(3-{3-[(2,2-Diphenyl-ethyl)-(3,5-di-tert-butyl-benzyl)-amino]-propoxy}-phenyl)-acetic acid (DY151). A solution of (3-{3-[(2,2-Diphenyl-ethyl)-(3,5-ditert-butyl-benzyl)-amino]-propoxy}-phenyl)-acetic acid methyl ester (4l). (0.56 g, 0.001 mol) in methanol (6 mL) was treated with 2N NaOH (4 mL) and the mixture stirred overnight at ambient temperature. After concentration to dryness, the residue was dissolved in EtOAc (15 mL) and water was added (5 mL), the solution acidified to pH 3 with concentrated hydrochloric acid, then extracted into EtOAc (3×20 mL). The combined organic extracts were dried over $Na_2SO_4$, and then concentrated in vacuo to provide the carboxylic acid as waxy oil, which was purified by flash chromatography (9:1 $CH_2Cl_2$/MeOH) to give the desired product as oil 0.42 g in 71% yield. $^1H$ NMR ($CD_3OD$) δ 7.31 (s, 1H), 7.17 (m, 7H), 7.16 (s, 1H), 7.12 (t, 2H), 7.11 (s, 3H), 6.84 (d, 1H), 6.58 (s, 1H), 6.56 (d, 1H), 4.24 (t, 1H), 3.81 (s, 2H), 3.64 (t, 2H), 3.51 (s, 2H), 3.26 (d, 2H), 2.78 (t, 2H), 1.86 (t, 2H); $^{13}C$ NMR ($CD_3OD$) δ 176.2, 160.3, 152.0, 144.4, 137.9, 130.2, 129.6, 129.2, 127.5, 125.0, 122.7, 122.6, 116.6, 114.1, 66.8, 61.0, 60.3, 52.6, 50.5, 42.8, 35.7, 32.0, 27.4. Anal. Calcd for $C_{40}H_{49}NO_3$: C, 81.18; H, 8.35; N, 2.37. Found: C, 81.27; H, 8.38; N, 2.22.

(3-{3-[(2,2-Diphenyl-ethyl)-(3,5-dimethoxy-benzyl)-amino]-propoxy}-phenyl)-acetic acid (DY152). A solution of (3-{3-[(2,2-Diphenyl-ethyl)-(3,5-dimethoxy-benzyl)-amino]-propoxy}-phenyl)-acetic acid methyl ester (4j). (0.26 g, 0.00047 mol) in methanol (3 mL) was treated with 2N NaOH (2 mL) and the mixture stirred overnight at ambient temperature. After concentration to dryness, the residue was dissolved in EtOAc (15 mL) and water was added (5 mL), the solution acidified to pH 3 with concentrated hydrochloric acid, then extracted into EtOAc (3×20 mL). The combined organic extracts were dried over $Na_2SO_4$, and then concentrated in vacuo to provide the carboxylic acid as waxy oil, which was purified by flash chromatography (9:1 $CH_2Cl_2$/MeOH) to give the desired product as oil 0.23 g in 92% yield. Solidification of the waxy oil from pet. ether gave white solid (5j), mp: 44.4° C. $^1H$ NMR ($CD_3OD$) δ 7.19 (d, 9H), 7.11 (m, 2H), 6.82 (d, 1H), 6.60 (s, 1H), 6.56 (d, 1H), 6.30 (s, 2H), 6.27 (s, 1H), 4.21 (t, 1H), 3.62 (t, 2H), 3.60 (s, 2H), 3.57 (s, 6H), 3.52 (s, 2H), 3.16 (d, 2H), 2.68 (t, 2H), 1.81 (t, 2H); $^{13}C$ NMR ($CD_3OD$) δ 176.0, 162.1, 160.4, 144.8, 143.7, 137.6, 130.2, 129.4, 129.3, 127.4, 122.5, 116.5, 114.1, 107.9, 100.6, 66.7, 60.8, 60.6, 55.7, 52.0, 50.9, 42.5, 27.7. Anal. Calcd for $C_{34}H_{37}NO_5$: C, 75.67; H, 6.91; N, 2.60. Found: C, 75.62; H, 6.94; N, 2.42.

{3-[3-(2,2-Diphenyl-ethylamino)-propoxy]-phenyl}-acetic acid (DY155). A solution of {3-[3-(2,2-Diphenyl-ethylamino)-propoxy]-phenyl}-acetic acid methyl ester (3) (0.03 g, 0.000074 mol) in methanol (3 mL) was treated with 2N NaOH (2 mL) and the mixture stirred overnight at ambient temperature. After concentration to dryness, the residue was dissolved in EtOAc (15 mL) and water was added (5 mL), the solution acidified to pH 3 with concentrated hydrochloric acid, then extracted into EtOAc (3×15 mL). The combined organic extracts were dried over $Na_2SO_4$, and then concentrated in vacuo to provide the carboxylic acid as waxy oil, which was purified by flash chromatography (9:1 $CH_2Cl_2$/MeOH) to give the desired product as a solid 0.025 g in 83% yield. Crystallization of the solid from EtOAc gave white crystals, mp: 49.1° C. $^1H$NMR ($CD_3OD$) δ 7.17 (m, 1H), 6.80 (d, 1H), 6.78 (d, 1H), 6.64 (s, 1H), 4.12 (t, 1H), 3.56 (s, 2H), 3.49 (t, 2H), 3.12 (d, 2H), 2.66 (t, 2H), 1.72 (t, 2H); $^{13}C$ NMR ($CD_3OD$) δ 176.0, 160.1, 143.5, 137.9, 130.4, 129.9, 129.1, 128.0, 122.9, 116.6, 113.9, 65.9, 60.1, 54.8, 51.9, 42.6, 26.3. Anal. Calcd for $C_{25}H_{27}NO_3 \cdot 2H_2O$: C, 70.56; H, 6.40; N, 3.29. Found: C, 70.58; H, 6.28; N, 3.20.

Example 7

Screening of Compound Library for LXRβ-Selective Activation

The compounds produced herein will be screened for activation of LXRα and LXRβ using a reporter gene assay in transiently transfected CV-1 cells. The approach will be the same as that described in Example 2, which was used to identify the LXRβ-selective ligands DY136 and DY142. Compounds will initially be tested at doses of 10 μM and the relative fold activation on LXRα and LXRβ will be determined. T0901317, GW3965, DY136 and DY142 may be included as positive controls. Compounds with promising activity in this initial screen will be retested and control experiments will be performed to confirm that the effect is LXR-mediated. Dose-response experiments will be performed on the most promising compounds and the selectivity-factor (LXRβ-fold activity/LXRα-fold activity) for LXRβ will be determined at each dose.

The transient transfection reporter gene assay has several advantages that make it ideal for this initial screen. These assays are routinely performed in 96-well plates using an automated Biomek workstation. Therefore, each compound can be rapidly tested in triplicate using only 3 plates for LXRα and 3 plates for LXRβ. This allows for rapid testing of the 96-member library. Another advantage to this cell-based transcription assay is that it inherently excludes compounds that are unlikely to be active in vivo. In contrast, in vitro biochemical assays can identify LXR ligands that may not be useful in vivo because they fail to cross membranes, are rapidly metabolized by cells, or are toxic.

The cell-based reporter assay reports a positive compound as one that activates LXR directly (i.e. via ligand binding pocket) or indirectly (e.g. by activating an unrelated pathway that converges on LXR). To confirm compounds that activate LXR directly, in vitro assays with purified LXR proteins are used. While radioligand displacement assays could in principle be used for this purpose, the one radioligand that has been studied (24(S),25-epoxycholesterol) is prohibitively expensive ($26,000/custom synthesis) and is difficult to work with as it is a low affinity ligand with high non-specific binding. Indeed, this is a common problem in the orphan nuclear receptor field. To overcome this limitation, numerous labs have used in vitro coactivator recruitment assays as surrogates for ligand binding. This assay takes advantage of the fact that ligand-occupied nuclear receptors undergo a conformation change that promotes association with a variety of coactivator peptides possessing an LXXLL peptide motif. Ligand binding activity is inferred when a compound promotes in vitro association of the receptor with a coactivator peptide. Indeed, the LXR ligands T0901317 and GW3965 were first identified in this matter[58]. Thus, we propose to use this approach to confirm the ligand binding activity of compounds identified in the initial reporter gene assay.

For example, Collins et al.[58] have shown that GW3965 promotes association of LXR with a coactivator peptide derived from SRC-1. Therefore, we will perform the coactivator recruitment assays using chimeric proteins containing GST fused to the SRC-1 receptor interaction domains. GST-SRC-1 will be incubated with [$^{35}$S]-LXR along with the test compound. Any complex that is formed will be isolated on glutathione-sepaharose beads and the amount [$^{35}$S]-LXR bound to the coactivator will be quantified.

Example 8

Validation of LXRβ-Selectivity on Endogenous Gene Expression

Once the most promising candidate compounds have been selected, their specificity for LXRβ will be tested by examining their effects on endogenous LXR target genes. Experiments will be performed in H4 (neuroglioma), SH-SY5Y (neuronal) and CCF-STTG1 (astrocytic) cell-lines. Cells will be treated for 6 to 25 hours with positive controls (T0901317, GW3965) and the selected test compounds. Gene expression is monitored by quantitative real time RT-PCR (QRT-PCR) as described in the preliminary data. We will follow expression of key targets involved in the "therapeutic" effect of and reducing Aβ and promoting cholesterol efflux (ABCA1, apoE) and in the negative side-effect of hypertriglyceridemia (SREBP1c, FAS). As demonstrated in the preliminary results, the LXRβ-selective ligands DY136 and DY142 exhibit the expected activation of ABCA1 with little effect on SREBP1c. We will also monitor the effect of these compounds on cholesterol efflux as described in section B.

The above studies will identify compounds that are active in several types. Two distinct models will be used to demonstrate that these activities are mediated via selective activation of LXR. RAW cells are a macrophage line that lacks LXRα. RAW cell-derivatives engineered by Dr. Peter Tontonoz will be used to overexpress each individual LXR subtype. Cells will be treated with control or test compounds and gene expression will be monitored by QRT-PCR. These RAW-LXRα and RAW-LXRβ will provide a useful means to specifically link the activity of our compounds to each individual LXR-subtype and to confirm LXRβ-selective activity on endogenous gene activity.

Candidate compounds will also be tested in H4 and SH-SY5Y cells made deficient for LXRα and/or LXRβ by siRNA-mediated knock-down. Two independent siRNAs targeting LXRα and two that target LXRβ have been identified. All four of these siRNA yield 80% knock-down of their target gene with no effect on control transcripts. Furthermore, the combination of siRNA against LXRα and LXRβ dramatically reduces expression of ABCA1. The effects of each individual siRNA on ABCA1 expression are less impressive, as both subtypes can regulate this target gene. These results validate the utility of these siRNAs as the results are in concordance with data gleaned from LXRα-, LXRβ- and LXRα/β double knockout mice.

Gene expression and cholesterol efflux studies will be performed as described in the preliminary data. For siRNA-mediated knock-down of LXR cells are transfected with vehicle control or 10 nM of siRNA targeting LXRβLXRβ, or both LXRα/β in OptiMEM medium using Lipofectamine 2000 (Invitrogen). Transfection is terminated four hours later by addition of 20% FBS medium and cell are collected for RNA analysis as described in the preliminary data.

Example 9

Validation of LXRβ-Selective Activity in Primary Glial Cultures from Wild-Type and LXR-Null Mice A relevant test of LXRβ specificity will be obtained by comparing activity in primary glial cells derived from wild-type, LXRα-null, LXRβ-null, and LXRα/β-null mice. Gene expression will be monitored as described above. We anticipate that the LXRβ-selective ligands will activate ABCA1 without activating SREBP1c. These studies will further assess the selectivity of compounds identified.

Glial cultures are prepared from 3 day-old mouse pups. Briefly, the cortex is gently tirturated and trypsinized and the cell-pellet resuspended and filtered through a 70 μm cell-strainer and plated in DMEM:F12:FBS (40:40:20) Cells are washed and media replaced the following day. Over a period of two weeks the serum content is decreased to 10%. The cultures are shaken twice for 2 hours (12 hours apart) and replated to yield>95% pure astrocyte cultures, as indicated by GFAP and vimentin expression[59].

LXRβ-selective ligands will be prioritized based on the following criteria: (1) strong stimulation of ABC-transporters and cholesterol efflux (2) minimal induction of SREBP1c and FAS (3) siRNAs directed at LXRβ lower the ABCA1/cholesterol-efflux effect, (4) glial cultures from LXRβ-knockout fail to respond (or respond poorly) to these drugs. LXRβ ligands that upregulate apoE expression will be of particular interest.

Example 10

LXRs and AD Therapy

Both LXR subtypes are expressed in the CNS at significant levels: LXRα mRNA levels range from 7-29% of that in the liver, while LXRβ levels are 2-5 fold higher in the brain than in liver. The levels of LXRα in cultured neurons and glia are 2% and 17% compared to the liver, and that for LXRβ are 1.1- and 3.8-fold, respectively[33]. These findings suggest that LXRβ is the predominant subtype in the CNS.

LXR ligands are active in CNS-derived cells and display many of gene expression patterns expected from the studies in peripheral cells including hepatocytes and macrophages. For example, treatment of primary neuronal and astrocyte cultures with T0901317 resulted in enhanced cholesterol efflux and increased expression of ABCA1, ABCG1, and SREBP1c[33]. Similarly, gene-expression studies in Lxrα/β-null mice demonstrated that LXRs regulate the same target genes in the brain including: ABCA1, ABCG1, ABCG5, ABCG8, SREBP1c and FAS[50]. LXR agonists are known to activate apoE in certain cell-types[51]. We have found that T0901317 increases apoE expression in H4 neuroglioma cells (see section C below) and it can do so in an astrocytoma cell-line as well[35]. It is unclear if LXRs regulate apoE expression throughout the brain as no apoE protein induction is seen when total brain lysates are analyzed[52]. While the effect of LXRs on apoE require additional study, it is clear that LXRs can induce a network of genes required for cholesterol- and phospholipid-efflux in the brain.

Given the known links between cholesterol, APP processing and AD, the observation that LXR increases cholesterol efflux via ABCA1 induction raised the possibility that LXR ligands could directly reduce Aβ-production. Indeed, this hypothesis has now been reported by several groups. For example, activation of LXRs in human neuroblastoma cell-lines increased ABCA1 expression, enhanced cholesterol efflux and reduced Aβ production[34]. Similarly, T0901317 treatment enhanced ABCA1 expression and decreased Aβ production in mouse Neuro2A cells expressing human APPswe[36] and in mouse primary neuronal cultures transduced with human-APP[53]. This decrease in Aβ production could be mimicked by overexpression of wild-type ABCA1 but not by a mutant that was defective in cholesterol transport and apoAI binding[36]. Similar findings have recently been reported in vivo: one-week treatment of transgenic mice expressing human APPswe with T0901317 resulted in a significant decrease in Aβ40 and Aβ42 in the brain[52].

While these the majority of research groups have found similar effects of LXR ligands on Aβ production, Fukumoto et al.[54] have reported opposing results. Their conclusion is that LXR-mediated ABCA1 induction increases Aβ levels. In their Aβ studies, cells were co-treated with LXR ligands and 9-cis retinoic acid, a promiscuous ligand that binds to the nuclear receptors RXRα,β,γ and RARα,β,γ. RXRs act as obligate heterodimers for LXR and numerous other nuclear receptors. Thus, depending on the receptors expressed in their cells, it is possible that Fukumoto et al.[54] observed the combined actions of multiple receptor pathways. Hence, this finding represents an experimental paradigm that is entirely distinct from our current proposal as we do not propose any combined treatments with RXR ligands.

Taken together, these observations provide strong evidence that LXR activation in the CNS can reduce production of the amyloidogenic Aβ peptide[52]. These effects are autonomous to the CNS and require LXR-dependent activation of ABCA1[36,52]. Thus, LXR activation can raise HDL-cholesterol, reduce atherosclerosis in the peripheral vasculature, and can independently control neuronal production of Aβ. These observations suggest that LXR represents an exciting new molecular target for the treatment of AD and atherosclerosis. Indeed, like most nuclear receptors, LXR is readily "druggable" as it recognizes low molecular weight compounds (300-500 Da) and is amenable to high-throughput screens. While non-selective LXRα/β pan-agonists already exist, effective clinical development of LXR ligands for AD therapy will require dissociation of the Aβ-lowering effects from the negative side-effects of hypertriglyceridemia. Since LXRβ is highly expressed in the brain and since this subtype can stimulate ABCA1 and cholesterol efflux, it is tantalizing to suggest that LXRβ-selective ligands may represent an ideal therapy for decreasing Aβ production in the CNS.

Example 11

Effects of LXRβ-Selective Compounds on Aβ Production, APP Processing and Aβ Clearance It is our current observation and understanding that LXR ligands (e.g., LXR agonists) decrease Aβ production via an ABCA1-dependent cholesterol efflux pathway. In the setting of AD, the accumulation of amyloid plaques is a more complex process that is likely to represent the net effect of several factors including Aβ production, APP processing and the clearance of Aβ. In order for a therapeutic agent to be effective against AD, it must have a net positive effect on the summation of these events. Thus, to further characterize the potential clinical utility of LXR selective compounds prior to animal testing, the effects of LXRβ-selective ligands on Aβ production, APP processing and Aβ clearance need to be examined.

Several lines of evidence suggest that changes in cellular cholesterol content may modulate critical steps in APP processing and Aβ production. For example, access of α- and β-secretase to APP is thought to be a rate-limiting step[60], and reduction in cellular cholesterol is thought to shift APP processing away from the amyloidogenic β-secretase in favor of the non-amyloidogenic α-secretase pathway. In order to characterize the potential effect of our LXRβ-selective compounds on these processes, we will monitor individual steps in the mediated cleavage of APP. In cell-culture, processing of APP by α- or β-secretase cleave the N-terminal APP fragment and release it into the medium. These N-terminal fragments are known as sAPPα or sAPPβ. Specifically, we will monitor the following end-points: secreted-APPα and sAPPβ into the media, APP processing within cells, and Aβ levels in both media and lysates.

All the proposed experiments will be performed in H4 and SH-SY5Y cells plated in 6-well or 150-mm plates. One day after plating, cells will be treated with 0.01×, 0.1× and 1× concentrations of the most promising LXRβ ligands (1×=optimal concentration based on ligand-activated transcription, specific aim 1). Twenty-four hours later the media will be collected and processed for Aβ ELISAs as described in the preliminary data and for sAPP-detection via western blot. APP fragments in the medium will be detected with the following antibodies: sAPPα-6E10; sAPPβ-APP B5-5313; sAPPα/β-22C11. For cell-lysates, we will use 22C11 to identify $APP_{full-length}$, sAPPβ, sAPPα, and immature APP; O443 to identify all APP fragments containing the CTF; and anti-GAPDH as loading control.

For quantification of the intracellular Aβ, cells are scraped and lysed in 70% formic acid. Larger 150 mm plates are used for this assay as intracellular Aβ levels are relatively low and more cells are required (preliminary data). The lysates are dried using a speedvac, resuspended in 2% Na2CO3/0.1 N NaOH with protease inhibitors and assayed for Aβ40 and Aβ42 by ELISA[61].

Since reduction of membrane cholesterol content increases APP processing by α-secretase, it is contemplated that LXRβ-selective ligands will increase cholesterol efflux and shift APP processing from the α- to α-secretase pathway. This will in turn reduce Aβ and sAPPβ, and increase sAPPα release from these cells. Western-blotting for APP in the cell-lysates will determine if the shift from β- to α-secretase cleavage is a secondary consequence of diminished endogenous APP levels.

The accumulation of amyloid plaques is a function of both Aβ production and clearance, and LXR may regulate genes that are critical for Aβ clearance. Specifically, LXR ligands have been shown to induce apoE in certain cells types. Clearance of amyloid plaque by astrocytes in vitro is blocked by antibodies against apoE, Aβ, and by Receptor Associated Protein (RAP) which blocks receptors of the LDLR-family. ApoE is known to be an avid Aβ-binder. Taken together, this suggests that apoE is required for plaque clearance via the following mechanism. ApoE secreted by astrocytes binds to Aβ, "recruits" astrocytes to the deposits and promotes plaque-phagocytosis via LDLR or LRP[62]. LXRβ ligands stimulate ApoE expression (preliminary data) and LXRβ ligands are known to increase apoE protein levels by stabilizing it through ABCA1[39,40]. Thus, LXRβ ligands could promote plaque clearance by activating apoE expression. We will test this possibility by measuring the effects of LXRβ ligands on Aβ uptake and on plaque clearance. It is contemplated that astrocytes treated with LXRβ ligands may secrete more apoE which could accentuate Aβ-plaque clearance.

In the plaque clearance assay, brains from sixteen month old Tg2576 mice expressing human APPswe will be harvested and frozen on dry-ice. Ten μm sagittal sections will be cut and collected onto poly-L-Lysine coated coverslips. The brain sections are placed in a 2-chamber slide and astrocytes are plated on top at a density of 50,000 cells/chamber in serum-free medium supplemented with ITS[62]. The experiment will compare Aβ-clearance from four adjacent sections: ±astrocytes, ±LXRβ ligands. Twenty-four hours later the conditioned medium is used for apoE measurement (western blots). The cells+sections are fixed with 4% paraformaldehyde and processed for GFAP and Aβ (6E10, Aβ40- and Aβ42 specific antibodies) double-immunofluorescence. 3-Dimensional z-stacks will be acquired using Zeiss LSM510 Axioplan-2 microscope equipped with two-photon Ti-Sapphire pulse laser. The images will be reconstructed and segmented using automated and interactive algorithms in the AmiraVis software (Neuroscience Light Microscopy core at City of Hope). The volume of Aβ phagocytosed by GFAP-labeled astrocytes, and Aβ in the brain-section (astrocytes segmented out) will be quantified from the 3D segmented images.

Primary astrocyte cultures are established as previously reported by us[59]. Three month old C57BL/6 mice will be terminally anesthetized with isoflurane and the brains will be isolated. Cortex will be dissected away from rest of the tissue and cut into ~1 mm³ pieces, and processed as described[59] (appendix).

Example 12

Administering LXRβ-Selective Compounds to Tg2576 Transgenic Mice Overexpressing Human APPswe Tg2576 mice provide a well-established model for these studies because the overexpress human-APP with the familial Swedish mutation (KM-670/671-NL). These mice start developing AD-like neuritic plaques at about 10 months of age and plaque formation increases exponentially with age[65]. In addition to the neuritic plaques, oligomeric and protofibrillar forms of Aβ have also been implicated in memory loss and neurotoxicity[3,66]. It is believed that these multimeric forms are produced by Aβ42 acting as nucleating-factor with additional Aβ40/42 being added onto the "seed". Further aggregation of these multimers leads to plaque deposition. Thus, drugs that attenuate Aβ-production would reduce Aβ-oligomers, protofibrils, and plaque deposition. It is contemplated that the effects of LXRβ selective compounds are evaluated on Aβ-production, Aβ-deposition, and plaque clearance in Tg2576 mice.

A prerequisite for performing useful drug studies in animals is to determine the optimal and preferred route of delivery. This experiment will determine the optimal dosage and delivery method of two LXRβ ligands for the subsequent experiments in Tg2576 mice. We aim to identify a dose that can maintain 75-100% of maximal response on ABCA1 expression in the neocortex and hippocampus.

In performing the experiment, C57BL/6 mice will be administered potential LXRβ drugs or vehicle by subcutaneous injection (vehicle is PBS), or oral gavage (0.5% methylcellulose) with a single dose of 100 mg/kg (n=4/group). The mice will be euthanized by CO2 asphyxiation 8- or 24-hours later and the liver and brain will be dissected for RNA isolation. Induction of ABCA1 and/or other LXR target genes will be monitored to determine the optimal delivery method. The time-course may have to be extended to identify optimal frequency (48 72, and 96 hours). Subsequently, a dose-response curve for induction of these target-genes will be generated after delivery of 1, 10 and 100 mg/kg using the previously determined treatment method and time-point (n=4 per group). Based on these results we will estimate the daily dose required to maintain ABCA1 expression in the neocortex and hippocampus to 75-100% of maximal response. This treatment paradigm will be tested for 1 week in adult C57BL/6 and Tg2576 mice (n=4/group) to identify any differences in induction of ABCA1 between the two genetic backgrounds. We will test a comparable dose in mice for 4 weeks by either admixing the drug with food or via mini-osmotic pump. The advantage of admixing the drug with food or delivery via a mini-osmotic pump is that it minimizes animal handling, injury and stress during the course of the long-term study.

If the most interesting LXRβ ligands from in vitro studies is without an effect in brain with the above listed delivery methods, then we will study the effect of this compound by direct delivery into the third ventricle. The mice will be anesthetized with ketamine/xylazine/NaCl cocktail (20 ml/kg). The mouse will be prepared for stereotaxic surgery. Initial optimization will be by a single injection using dose (50-fold lower amount) and time comparable to that described above. The injection coordinates are −0.3 mm (AB), 3 mm (DV) at midline relative to bregma[67]. We have used this technique as well as implantation of a brain-infusion kit with mini-osmotic pump to delivery Aβ-oligomers into rat-brain[68]. Intracerebral delivery will be used as the last option.

It is contemplated that the above experiments will determine the dose and route of delivery required to activate LXRβ-dependent gene expression in the brain. These studies will also be useful to confirm that LXRβ ligands do not promote in vivo induction of SREBP1c or FAS in liver.

Example 13

Effect of LXRβ-Selective Compounds on Aβ-Production in Tg2576 Mice

Aβ is needed for transformation of the "Aβ42 seed" into oligomers and protofibrils, and further aggregation into plaques. Thus, early attenuation of Aβ levels is considered a key target in AD-therapy. This experiment tests the effects of novel LXRβ ligands on circulating lipids and steady-state Aβ40 and Aβ42 in the brains of young Tg2576 mice, i.e. those that have not yet developed AD-pathology.

LXRβ compounds will be delivered for 2 weeks to 6 month old Tg2576 male mice using the optimal dose and method determined above (n=10/group; groups: drug1, drug2, and vehicle). Blood samples will be collected in lithium-heparinized tubes (60 μl, tail-bleed) prior to the treatment (baseline), once during the course of the treatment (7 days), and at the end of the experiment (14 days) from awake mice as anesthesia has a rapid effect on some of these parameters (unpublished data). Blood collection will be at the same predetermined time for all the studies to minimize diurnal variations. Plasma (~25 μl) is isolated by centrifugation and assayed for triglycerides, free fatty-acids, cholesterol, and glucose (≤5 μl per assay). These assays are well established in the lab. After the last blood collection, the mice will be euthanized by halothane and transcardially perfused with 100 ml of PBS. The brain is isolated and neocortex, hippocampus and cerebellum are micro-dissected from both hemispheres (cerebellum is "control" for AD-pathology; other regions do not show significant pathology). Regions from one hemisphere will be used for AD- and LXR-related biochemistry (westerns). Regions from the other hemisphere will be cut in half and used for gene-expression analysis and Aβ ELISAs. There is no brain pathology at this age so histology is not included for this section. Other tissues to be collected are liver, intestine, fat and kidney. These tissues will be processed for gene-expression analysis to identify potential "side-effects" and possible confounds.

Brain regions saved for biochemistry will be homogenized in cold PBS containing protease inhibitor cocktail (4× volume), boiled with Laemmli SDS-PAGE loading dye and 20 μg is electrophoresed on 6-12% gels[69]. For quantification of soluble+insoluble Aβ40 and Aβ42, the brain regions will be homogenized in 8-volumes of 5 M guanidine-HCl, 50 mM Tris (pH 8.0) containing protease inhibitor cocktail, and mixed for 4 hours at room temperature[70]. The samples will be centrifuged at 14,000×g for 20 min at 4° C. The supernatant will be diluted 10-fold in PBS (pH 7.4) containing 5% BSA and 0.03% Tween-20[70] and assayed for Aβ40 and Aβ42.

It is possible that the selected LXRβ ligands may not cross the blood-brain barrier and therefore may not induce LXR-target genes in the brain. In this case, the ligands are delivered via intracerebroventricular (ICV) infusion. A mini-osmotic pump will be loaded with the LXRβ ligand (vehicle is artificial CSF+DMSO). Mice will be anesthetized and a pre-assembled "cannula+connector-tube+mini-osmotic pump" is slid posteriorly such that the pump sits sub-dermally behind the clavicles. The 30-gauge cannula itself is 3 mm deep and sufficiently long for the tip to be in the ventricles. The assembled cannula is less than 5 mm in height (after the holder is removed). The newer brain-infusion cannula has a wider-flat base that is superglued directly to the skull (Kit 3, Alzet). For the two-week delivery period we will use mini-osmotic pump that deliver at a rate of 0.25 μl/hr (1002, Alzet). We have done similar cannula-pump implantation surgeries in rats[68]. This procedure provides an alternative delivery method.

It is contemplated that LXRβ-selective compounds will be effective at reducing steady-state Aβ levels in the brain for the same reasons as described in specific aim 2a. It is further contemplated that the APPα:APPβ ratio will increase in mice treated with LXR ligands. However, LXRβ selective compounds will not dramatically alter plasma lipid-profile or induce SREBP1c.

Example 14

Effect of LXRβ-Selective Compounds on Aβ-Deposition in Tg2576 Mice

Plaque formation is an ongoing process that reflects the opposing effects of deposition and clearance. Plaque dynamics in human subjects and AD-mouse models are relatively slow compared to the rapid events of APP proteolytic processing. Thus in a clinical setting, chronic treatment would presumably be required to maintain a beneficial effect on plaque-deposition. This experiment will examine whether LXRβ-selective drugs can reduce Aβ-deposition in Tg2576 mice that are just starting to deposit Aβ in the brain.

LXRβ compounds will be administered to 11-month old Tg2576 male mice for four weeks as above (n=10/group; groups are as in 3B). Blood samples (0, 7, 14, 21 & 28 days) and tissues will be collected as above. One hemisphere of the brain will be used for gene-expression analysis and Aβ ELISAs. The other hemisphere will be fixed in 4% paraformaldehyde (phosphate buffered, pH 7.4) by immersion and used for immunohistochemistry as previously described by us[71,72] (appendix). We will assess amyloid-deposition (Thioflavin-S), Aβ-deposition (Aβ$_{1-x}$;6E10), GFAP (astrocytes), NeuN (neurons), CD68 (activated microglia), and CD11b (all microglia). Double-immunofluorescent-labeling will be performed for 6E10 or ABCA1 with cell-specific markers. Amyloid and Aβ-deposits will be quantified as described by us[71] (appendix).

Based on the fact that LXR ligands reduce Aβ production, it is contemplated that the LXRβ ligands will attenuate amyloid and Aβ-deposition. LXR activation has anti-inflammatory potential[73], and thus LXRβ-drugs could also modulate glial activity surrounding Aβ-plaques[71,74,75]. It is contemplated that ABCA1 will be activated in multiple cell-types. At this point qualitative assessment of ABCA1 induction in neurons would be adequate to support the concept, i.e. LXRβ induced activation of ABC-transporters reduces membrane-cholesterol levels in neurons and consequently reduces Aβ-production and Aβ-deposition.

Example 15

Evaluating Whether LXRβ Ligand Reverse AD-Like Pathology in Tg2576 Mice

As mentioned above, LXRβ ligands can reduce Aβ production and may potentially increase Aβ clearance via apoE. Thus, LXRβ ligands may have the potential to reverse AD-like pathology in older Tg2576 mice.

To confirm this, sixteen month old Tg2576 male mice will be treated with LXRβ-drugs for a period of 1 month as above (n=10/group); groups: drug1, drug2, vehicle, and 1 month younger untreated mice). It is contemplated that LXRβ ligands which reduce Aβ, and may also reverse AD-like pathology. This will be ascertained by comparison of AD-like pathology in the 17-month old LXRβ-ligand treated mice with 16-month old untreated mice. This would represent a net positive effect on the combined processed of Aβ-production, deposition and clearance. These findings would provide clear evidence to support the development of LXRβ ligands in treatment of Alzheimer's Disease.

REFERENCES

1. Wong, C. W., V. Quaranta & G. G. Glenner. 1985. Neuritic plaques and cerebrovascular amyloid in Alzheimer disease are antigenically related. Proc Natl Acad Sci USA. 82: 8729-32.
2. Masters, C. L., G. Simms, N. A. Weinman, G. Multhaup, B. L. McDonald & K. Beyreuther. 1985. Amyloid plaque core protein in Alzheimer disease and Down syndrome. Proc Natl Acad Sci USA. 82: 4245-9.
3. Hardy, J. & D. J. Selkoe. 2002. The amyloid hypothesis of Alzheimer's disease: progress and problems on the road to therapeutics. Science. 297: 353-6.
4. Kojro, E., G. Gimpl, S. Lammich, W. Marz & F. Fahrenholz. 2001. Low cholesterol stimulates the nonamyloidogenic pathway by its effect on the alpha-secretase ADAM 10. Proc Natl Acad Sci USA. 98: 5815-20.
5. Kinoshita, A., H. Fukumoto, T. Shah, C. M. Whelan, M. C. Irizarry & B. T. Hyman. 2003. Demonstration by FRET of BACE interaction with the amyloid precursor protein at the cell surface and in early endosomes. J Cell Sci. 116: 3339-46. Epub 2003 Jun. 26.
6. Ehehalt, R., P. Keller, C. Haass, C. Thiele & K. Simons. 2003. Amyloidogenic processing of the Alzheimer beta-amyloid precursor protein depends on lipid rafts. J. Cell Biol. 160: 113-23.
7. Riddell, D. R., G. Christie, I. Hussain & C. Dingwall. 2001. Compartmentalization of beta-secretase (Asp2) into low-buoyant density, noncaveolar lipid rafts. Curr Biol. 11: 1288-93.
8. Marlow, L., M. Cain, M. A. Pappolla & K. Sambamurti. 2003. Beta-secretase processing of the Alzheimer's amyloid protein precursor (APP). J Mol. Neurosci. 20: 233-9.
9. He, X., F. Li, W. Chang & J. Tang. 2004. GGA proteins mediate the recycling pathway of memapsin 2 (BACE). J Biol. Chem. 21: 21.
10. Vetrivel, K. S., H. Cheng, W. Lin, T. Sakurai, T. Li, N. Nukina, P. C. Wong, H. Xu & G. Thinakaran. 2004. Association of gamma-secretase with lipid rafts in post-Golgi and endosome membranes. J. Biol. Chem. 279:44945-54. Epub 2004 Aug. 17.
11. Wahrle, S., P. Das, A. C. Nyborg, C. McLendon, M. Shoji, T. Kawarabayashi, L. H. Younkin, S. G. Younkin & T. E. Golde. 2002. Cholesterol-dependent gamma-secretase activity in buoyant cholesterol-rich membrane microdomains. Neurobiol Dis. 9: 11-23.
12. Neufeld, E. B., A. M. Cooney, J. Pitha, E. A. Dawidowicz, N. K. Dwyer, P. G. Pentchev & E. J. Blanchette-Mackie. 1996. Intracellular trafficking of cholesterol monitored with a cyclodextrin. J Biol. Chem. 271:21604-13.
13. Carstea, E. D., J. A. Morris, K. G. Coleman, S. K. Loftus, D. Zhang, C. Cummings, J. Gu, M. A. Rosenfeld, W. J. Pavan, D. B. Krizman, J. Nagle, M. H. Polymeropoulos, S. L. Sturley, Y. A. Toannou, M. E. Higgins, M. Comly, A. Cooney, A. Brown, C. R. Kaneski, E. J. Blanchette-Mackie, N. K. Dwyer, E. B. Neufeld, T. Y. Chang, L. Liscum, D. A. Tagle & et al. 1997. Niemann-Pick C1 disease gene: homology to mediators of cholesterol homeostasis. Science. 277: 228-31.
14. Yamazaki, T., T. Y. Chang, C. Haass & Y. Ihara. 2001. Accumulation and aggregation of amyloid beta-protein in late endosomes of Niemann-pick type C cells. J Biol. Chem. 276: 4454-60. Epub 2000 Nov. 20.
15. Burns, M., K. Gaynor, V. Olm, M. Mercken, J. LaFrancois, L. Wang, P. M. Mathews, W. Noble, Y. Matsuoka & K. Duff. 2003. Presenilin redistribution associated with aberrant cholesterol transport enhances beta-amyloid production in vivo. J. Neurosci. 23: 5645-9.
16. Runz, H., J. Rietdorf, I. Tomic, M. de Bernard, K. Beyreuther, R. Pepperkok & T. Hartmann. 2002. Inhibition of intracellular cholesterol transport alters presenilin localization and amyloid precursor protein processing in neuronal cells. J. Neurosci. 22: 1679-89.
17. Jick, H., G. L. Zornberg, S. S. Jick, S. Seshadri & D. A. Drachman. 2000. Statins and the risk of dementia. Lancet. 356: 1627-31.
18. Wolozin, B., W. Kellman, P. Ruosseau, G. G. Celesia & G. Siegel. 2000. Decreased prevalence of Alzheimer disease associated with 3-hydroxy-3-methyglutaryl coenzyme A reductase inhibitors. Arch Neurol. 57: 1439-43.
19. Evans, R. M., C. L. Emsley, S. Gao, A. Sahota, K. S. Hall, M. R. Farlow & H. Hendrie. 2000. Serum cholesterol, APOE genotype, and the risk of Alzheimer's disease: a population-based study of African Americans. Neurology. 54: 240-2.
20. Jarvik, G. P., E. M. Wijsman, W. A. Kukull, G. D. Schellenberg, C. Yu & E. B. Larson. 1995. Interactions of apolipoprotein E genotype, total cholesterol level, age, and sex in prediction of Alzheimer's disease: a case-control study. Neurology. 45: 1092-6.
21. Notkola, I. L., R. Sulkava, J. Pekkanen, T. Erkinjuntti, C. Ehnholm, P. Kivinen, J. Tuomilehto & A. Nissinen. 1998. Serum total cholesterol, apolipoprotein E epsilon 4 allele, and Alzheimer's disease. Neuroepidemiology. 17: 14-20.
22. Scacchi, R., L. De Bernardini, E. Mantuano, T. Vilardo, L. M. Donini, M. Ruggeri, A. T. Gemma, R. Pascone & R. M. Corbo. 1998. DNA polymorphisms of apolipoprotein B and angiotensin I-converting enzyme genes and relationships with lipid levels in Italian patients with vascular dementia or Alzheimer's disease. Dement Geriatr Cogn Disord. 9: 186-90.
23. Kuo, Y. M., M. R. Emmerling, C. L. Bisgaier, A. D. Essenburg, H. C. Lampert, D. Drumm & A. E. Roher. 1998. Elevated low-density lipoprotein in Alzheimer's disease correlates with brain abeta 1-42 levels. Biochem Biophys Res Commun. 252: 711-5.
24. Moroney, J. T., M. X. Tang, L. Berglund, S. Small, C. Merchant, K. Bell, Y. Stem & R. Mayeux. 1999. Low-density lipoprotein cholesterol and the risk of dementia with stroke. Jama. 282: 254-60.
25. Reitz, C., M. X. Tang, J. Luchsinger & R. Mayeux. 2004. Relation of plasma lipids to Alzheimer disease and vascular dementia. Arch Neurol. 61: 705-14.
26. Launer, L. J., L. R. White, H. Petrovitch, G. W. Ross & J. D. Curb. 2001. Cholesterol and neuropathologic markers of AD: a population-based autopsy study. Neurology. 57: 1447-52.
27. Sparks, D. L., H. Liu, S. W. Scheff, C. M. Coyne & J. C. Hunsaker, 3rd. 1993. Temporal sequence of plaque formation in the cerebral cortex of non-demented individuals. J Neuropathol Exp Neurol. 52: 135-42.
28. Roher, A. E., C. Esh, T. A. Kokjohn, W. Kalback, D. C. Luehrs, J. D. Seward, L. I. Sue & T. G. Beach. 2003. Circle of willis atherosclerosis is a risk factor for sporadic Alzheimer's disease. Arterioscler Thromb Vasc Biol. 23: 2055-62. Epub 2003 Sep. 25.
29. Roher, A. E., C. Esh, A. Rahman, T. A. Kokjohn & T. G. Beach. 2004. Atherosclerosis of cerebral arteries in Alzheimer disease. Stroke. 35: 2623-7. Epub 2004 Sep. 16.
30. Tontonoz, P. & D. J. Mangelsdorf. 2003. Liver X receptor signaling pathways in cardiovascular disease. Mol. Endocrinol. 17: 985-93. Epub 2003 Apr. 10.

31. Repa, J. J. & D. J. Mangelsdorf. 2002. The liver X receptor gene team: potential new players in atherosclerosis. Nat. Med. 8: 1243-8.
32. Joseph, S. B. & P. Tontonoz. 2003. LXRs: new therapeutic targets in atherosclerosis? Curr Opin Pharmacol. 3: 192-7.
33. Whitney, K. D., M. A. Watson, J. L. Collins, W. G. Benson, T. M. Stone, M. J. Numerick, T. K. Tippin, J. G. Wilson, D. A. Winegar & S. A. Kliewer. 2002. Regulation of cholesterol homeostasis by the liver X receptors in the central nervous system. Mol. Endocrinol. 16: 1378-85.
34. Koldamova, R. P., I. M. Lefterov, M. D. Ikonomovic, J. Skoko, P. I. Lefterov, B. A. Isanski, S. T. DeKosky & J. S. Lazo. 2003. 22R-Hydroxycholesterol and 9-cis-Retinoic Acid Induce ATP-binding Cassette Transporter A1 Expression and Cholesterol Efflux in Brain Cells and Decrease Amyloid beta Secretion. J Biol. Chem. 278:13244-56.
35. Liang, Y., S. Lin, T. P. Beyer, Y. Zhang, X. Wu, K. R. Bales, R. B. DeMattos, P. C. May, S. D. Li, X. C. Jiang, P. I. Eacho, G. Cao & S. M. Paul. 2004. A liver X receptor and retinoid X receptor heterodimer mediates apolipoprotein E expression, secretion and cholesterol homeostasis in astrocytes. J. Neurochem. 88: 623-34.
36. Sun, Y., J. Yao, T. W. Kim & A. R. Tall. 2003. Expression of Liver X Receptor Target Genes Decreases Cellular Amyloid {beta} Peptide Secretion. J Biol. Chem. 278: 27688-27694.
37. Schaefer, E. J., C. B. Blum, R. I. Levy, L. L. Jenkins, P. Alaupovic, D. M. Foster & H. B. Brewer, Jr. 1978. Metabolism of high-density lipoprotein apolipoproteins in Tangier disease. N Engl J. Med. 299: 905-10.
38. Schaefer, E. J., D. W. Anderson, L. A. Zech, F. T. Lindgren, T. B. Bronzert, E. A. Rubalcaba & H. B. Brewer, Jr. 1981. Metabolism of high density lipoprotein subfractions and constituents in Tangier disease following the infusion of high density lipoproteins. J Lipid Res. 22: 217-28.
39. Hirsch-Reinshagen, V., S. Zhou, B. L. Burgess, L. Bernier, S. A. McIsaac, J. Y. Chan, G. H. Tansley, J. S. Cohn, M. R. Hayden & C. L. Wellington. 2004. Deficiency of ABCA1 impairs apolipoprotein E metabolism in brain. J Biol. Chem. 279:41197-207. Epub 2004 Jul. 21.
40. Wahrle, S. E., H. Jiang, M. Parsadanian, J. Legleiter, X. Han, J. D. Fryer, T. Kowalewski & D. M. Holtzman. 2004. ABCA1 is required for normal central nervous system ApoE levels and for lipidation of astrocyte-secreted apoE. J Biol. Chem. 279:40987-93. Epub 2004 Jul. 21.
41. Yu, L., J. York, K. von Bergmann, D. Lutjohann, J. C. Cohen & H. H. Hobbs. 2003. Stimulation of cholesterol excretion by the liver X receptor agonist requires ATP-binding cassette transporters G5 and G8. J Biol. Chem. 278: 15565-70. Epub 2003 Feb. 22.
42. Cao, G., T. P. Beyer, X. P. Yang, R. J. Schmidt, Y. Zhang, W. R. Bensch, R. F. Kauffman, H. Gao, T. P. Ryan, Y. Liang, P. I. Eacho & X. C. Jiang. 2002. Phospholipid transfer protein is regulated by liver X receptors in vivo. J Biol. Chem. 277: 39561-5. Epub 2002 Aug. 9.
43. Plosch, T., T. Kok, V. W. Bloks, M. J. Smit, R. Having a, G. Chimini, A. K. Groen & F. Kuipers. 2002. Increased hepatobiliary and fecal cholesterol excretion upon activation of the liver X receptor is independent of ABCA1. J Biol. Chem. 277: 33870-7. Epub 2002 Jul. 8.
44. Joseph, S. B., E. McKilligin, L. Pei, M. A. Watson, A. R. Collins, B. A. Laffitte, M. Chen, G. Noh, J. Goodman, G. N. Hagger, J. Tran, T. K. Tippin, X. Wang, A. J. Lusis, W. A. Hsuch, R. E. Law, J. L. Collins, T. M. Willson & P. Tontonoz. 2002. Synthetic LXR ligand inhibits the development of atherosclerosis in mice. Proc Natl Acad Sci USA. 99: 7604-9.
45. Schultz, J. R., H. Tu, A. Luk, J. J. Repa, J. C. Medina, L. Li, S. Schwendner, S. Wang, M. Thoolen, D. J. Mangelsdorf, K. D. Lustig & B. Shan. 2000. Role of LXRs in control of lipogenesis. Genes Dev. 14: 2831-8.
46. Peet, D. J., S. D. Turley, W. Ma, B. A. Janowski, J. M. Lobaccaro, R. E. Hammer & D. J. Mangelsdorf 1998. Cholesterol and bile acid metabolism are impaired in mice lacking the nuclear oxysterol receptor LXR alpha. Cell. 93: 693-704.
47. Repa, J. J., G. Liang, J. Ou, Y. Bashmakov, J. M. Lobaccaro, I. Shimomura, B. Shan, M. S. Brown, J. L. Goldstein & D. J. Mangelsdorf 2000. Regulation of mouse sterol regulatory element-binding protein-1c gene (SREBP-1c) by oxysterol receptors, LXRalpha and LXRbeta. Genes Dev. 14: 2819-30.
48. Horton, J. D., N. A. Shah, J. A. Warrington, N. N. Anderson, S. W. Park, M. S. Brown & J. L. Goldstein. 2003. Combined analysis of oligonucleotide microarray data from transgenic and knockout mice identifies direct SREBP target genes. Proc Natl Acad Sci USA. 100: 12027-32. Epub 2003 Sep. 25.
49. Repa, J. J., S. D. Turley, J. A. Lobaccaro, J. Medina, L. Li, K. Lustig, B. Shan, R. A. Heyman, J. M. Dietschy & D. J. Mangelsdorf. 2000. Regulation of absorption and ABC1-mediated efflux of cholesterol by RXR heterodimers. Science. 289: 1524-9.
50. Wang, L., G. U. Schuster, K. Hultenby, Q. Zhang, S. Andersson & J. A. Gustafsson. 2002. Liver X receptors in the central nervous system: from lipid homeostasis to neuronal degeneration. Proc Natl Acad Sci USA. 99: 13878-83.
51. Laffitte, B. A., J. J. Repa, S. B. Joseph, D. C. Wilpitz, H. R. Kast, D. J. Mangelsdorf & P. Tontonoz. 2001. LXRs control lipid-inducible expression of the apolipoprotein E gene in macrophages and adipocytes. Proc Natl Acad Sci USA. 98: 507-12. Epub 2001 Jan. 9.
52. Koldamova, R. P., I. M. Lefterov, M. Staufenbiel, D. Wolfe, S. Huang, J. C. Glorioso, M. Walter, M. G. Roth & J. S. Lazo. 2004. The LXR ligand T0901317 decreases amyloid beta production in vitro and in a mouse model of Alzheimer's disease. J Biol. Chem.
53. Brown, J., 3rd, C. Theisler, S. Silberman, D. Magnuson, N. Gottardi-Littell, J. M. Lee, D. Yager, J. Crowley, K. Sambamurti, M. M. Rahman, A. B. Reiss, C. B. Eckman & B. Wolozin. 2004. Differential expression of cholesterol hydroxylases in Alzheimer's disease. J Biol. Chem. 279: 34674-81. Epub 2004 May 17.
54. Fukumoto, H., A. Deng, M. C. Irizarry, M. L. Fitzgerald & G. W. Rebeck. 2002. Induction of the cholesterol transporter ABCA1 in central nervous system cells by liver X receptor agonists increases secreted Abeta levels. J Biol. Chem. 277: 48508-13.
55. Hoerer, S., A. Schmid, A. Heckel, R. M. Budzinski & H. Nar. 2003. Crystal structure of the human liver X receptor beta ligand-binding domain in complex with a synthetic agonist. J Mol. Biol. 334: 853-61.
56. Williams, S., R. K. Bledsoe, J. L. Collins, S. Boggs, M. H. Lambert, A. B. Miller, J. Moore, D. D. McKee, L. Moore, J. Nichols, D. Parks, M. Watson, B. Wisely & T. M. Willson. 2003. X-ray crystal structure of the liver X receptor beta ligand binding domain: regulation by a histidine-tryptophan switch. J Biol. Chem. 278: 27138-43. Epub 2003 May 7.

57. Lipinski, C. A., F. Lombardo, B. W. Dominy & P. J. Feeney. 2001. Experimental and computational approaches to estimate solubility and permeability in drug discovery and development settings. Adv Drug Deliv Rev. 46: 3-26.
58. Collins, J. L., A. M. Fivush, M. A. Watson, C. M. Galardi, M. C. Lewis, L. B. Moore, D. J. Parks, J. G. Wilson, T. K. Tippin, J. G. Binz, K. D. Plunket, D. G. Morgan, E. J. Beaudet, K. D. Whitney, S. A. Kliewer & T. M. Willson. 2002. Identification of a nonsteroidal liver X receptor agonist through parallel array synthesis of tertiary amines. J Med. Chem. 45: 1963-6.
59. Patel, N. V., M. Wei, A. Wong, C. E. Finch & T. E. Morgan. 2004. Progressive changes in regulation of apolipoproteins E and J in glial cultures during postnatal development and aging. Neurosci Lett. 371: 199-204.
60. Pedrini, S., T. L. Carter, G. Prendergast, S. Petanceska, M. E. Ehrlich & S. Gandy. 2005. Modulation of Statin-Activated Shedding of Alzheimer APP Ectodomain by ROCK. PLoS Med. 2: e18. Epub 2005 Jan. 11.
61. Kienlen-Campard, P., S. Miolet, B. Tasiaux & J. N. Octave. 2002. Intracellular amyloid-beta 1-42, but not extracellular soluble amyloid-beta peptides, induces neuronal apoptosis. J Biol. Chem. 277: 15666-70. Epub 2002 Feb. 22.
62. Koistinaho, M., S. Lin, X. Wu, M. Esterman, D. Koger, J. Hanson, R. Higgs, F. Liu, S. Malkani, K. R. Bales & S. M. Paul. 2004. Apolipoprotein E promotes astrocyte colocalization and degradation of deposited amyloid-beta peptides. Nat. Med. 10: 719-26. Epub 2004 Jun. 13.
63. Tokuda, T., M. Calero, E. Matsubara, R. Vidal, A. Kumar, B. Permanne, B. Zlokovic, J. D. Smith, M. J. Ladu, A. Rostagno, B. Frangione & J. Ghiso. 2000. Lipidation of apolipoprotein E influences its isoform-specific interaction with Alzheimer's amyloid beta peptides. Biochem J. 348: 359-65.
64. Dodart, J. C., R. A. Marr, M. Koistinaho, B. M. Gregersen, S. Malkani, I. M. Verma & S. M. Paul. 2005. Gene delivery of human apolipoprotein E alters brain A{beta} burden in a mouse model of Alzheimer's disease. Proc Natl Acad Sci USA. 102: 1211-6. Epub 2005 Jan. 18.
65. Kuo, Y. M., F. Crawford, M. Mullan, T. A. Kokjohn, M. R. Emmerling, R. O. Weller & A. E. Roher. 2000. Elevated A beta and apolipoprotein E in A betaPP transgenic mice and its relationship to amyloid accumulation in Alzheimer's disease. Mol. Med. 6: 430-9.
66. Klein, W. L., G. A. Kraffi & C. E. Finch. 2001. Targeting small Abeta oligomers: the solution to an Alzheimer's disease conundrum? Trends Neurosci. 24: 219-24.
67. Franklin, K. B. J. & G. Paxinos. 1997. The Mouse Brain in Stereotaxic Coordinates. Academic Press. San Diego.
68. Patel, N. V., A. C. P., M. T. E., R. I. & F. C. E. 2001. Caloric restriction attenuates inflammation in the brain after infusion of Abeta-derived diffusible ligands into the ventricles. Society for Neuroscience. 327.9.
69. Kalback, W., M. D. Watson, T. A. Kokjohn, Y. M. Kuo, N. Weiss, D. C. Luehrs, J. Lopez, D. Brune, S. S. Sisodia, M. Staufenbiel, M. Emmerling & A. E. Roher. 2002. APP transgenic mice Tg2576 accumulate Abeta peptides that are distinct from the chemically modified and insoluble peptides deposited in Alzheimer's disease senile plaques. Biochemistry. 41: 922-8.
70. Masliah, E., E. Rockenstein, I. Veinbergs, Y. Sagara, M. Mallory, M. Hashimoto & L. Mucke. 2001. beta-amyloid peptides enhance alpha-synuclein accumulation and neuronal deficits in a transgenic mouse model linking Alzheimer's disease and Parkinson's disease. Proc Natl Acad Sci USA. 98: 12245-50. Epub 2001 Sep. 25.
71. Patel, N. V., M. N. Gordon, K. E. Connor, R. A. Good, R. W. Engelman, J. Mason, D. G. Morgan, T. E. Morgan & C. E. Finch. 2005. Caloric Restriction Slows Amyloid Accumulation in Transgenic Models of Alzheimer Disease. Neurobiology of Aging. in press.
72. Patel, N., B. Hitzemann & R. Hitzemann. 1998. Genetics, haloperidol, and the Fos response in the basal ganglia: a comparison of the C57BL/6J and DBA/2J inbred mouse strains. Neuropsychopharmacology. 18: 480-91.
73. Ricote, M., A. F. Valledor & C. K. Glass. 2004. Decoding transcriptional programs regulated by PPARs and LXRs in the macrophage: effects on lipid homeostasis, inflammation, and atherosclerosis. Arterioscler Thromb Vasc Biol. 24: 230-9. Epub 2003 Oct. 30.
74. Yang, F., G. P. Lim, A. N. Begum, O. J. Ubeda, M. R. Simmons, S. S. Ambegaokar, P. P. Chen, R. Kayed, C. G. Glabe, S. A. Frautschy & G. M. Cole. 2004. Curcumin inhibits formation of Abeta oligomers and fibrils and binds plaques and reduces amyloid in vivo. J Biol. Chem. 7: 7.
75. Lim, G. P., F. Yang, T. Chu, E. Gahtan, O. Ubeda, W. Beech, J. B. Overmier, K. Hsiao-Ashec, S. A. Frautschy & G. M. Cole. 2001. Ibuprofen effects on Alzheimer pathology and open field activity in APPsw transgenic mice. Neurobiol Aging. 22: 983-91.
76. Sambrook et al., Molecular Cloning: A Laboratory Manual, $2^{nd}$ Ed., Cold Spring Harbor Laboratory Press, Cold Spring Harbor, N.Y.

What is claimed is:

1. An LXRβ-selective ligand having the formula:

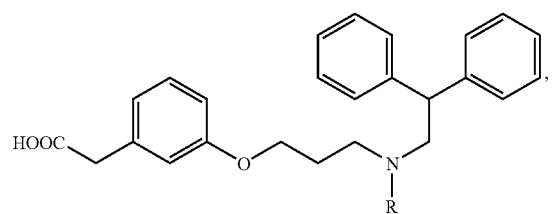

wherein R is

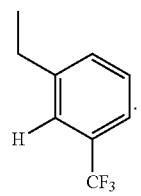

2. A pharmaceutical composition comprising a therapeutically effective amount of an LXRβ-selective ligand and a pharmaceutically acceptable carrier, wherein the LXRβ-selective ligand has the formula:

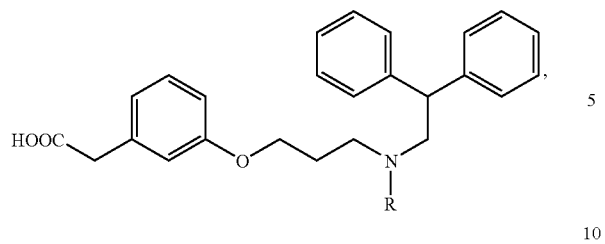
wherein R is
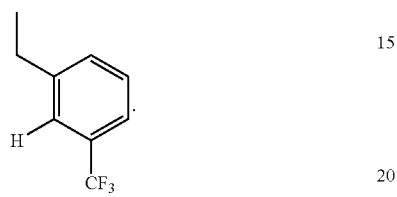
3. The LXRβ-selective ligand of claim 1, wherein the LXRβ-selective ligand is 3.4-6.5 fold selective for LXRβ over LXRα.
4. The pharmaceutical composition of claim 2, wherein the LXRβ-selective ligand is 3.4-6.5 fold selective for LXRβ over LXRα.
* * * * *